US008426358B2

(12) United States Patent
Kayser et al.

(10) Patent No.: US 8,426,358 B2
(45) Date of Patent: Apr. 23, 2013

(54) METHODS FOR TREATING ATHEROSCLEROSIS

(75) Inventors: Frank Kayser, San Francisco, CA (US); Marc Labelle, Chatham, NJ (US); Bei Shan, Redwood City, CA (US); Jian Zhang, Foster City, CA (US); Mingyue Zhou, Hayward, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/087,261

(22) Filed: Apr. 14, 2011

(65) Prior Publication Data

US 2011/0206652 A1 Aug. 25, 2011

Related U.S. Application Data

(62) Division of application No. 11/823,251, filed on Jun. 26, 2007, now abandoned.

(60) Provisional application No. 60/816,415, filed on Jun. 26, 2006.

(51) Int. Cl.
*A61K 38/00* (2006.01)
*A61P 9/10* (2006.01)
*C07K 14/47* (2006.01)

(52) U.S. Cl.
USPC ............................................ 514/1.1; 514/1.9

(58) Field of Classification Search ........................ None
See application file for complete search history.

(56) References Cited

U.S. PATENT DOCUMENTS

| | | | | |
|---|---|---|---|---|
| 6,498,019 | B1 * | 12/2002 | Taniyama | 435/69.1 |
| 6,596,544 | B1 | 7/2003 | Fogelman et al. | |
| 6,635,614 | B1 | 10/2003 | Santamarina-Fojo et al. | |
| 6,692,909 | B1 | 2/2004 | Lander et al. | |
| 2005/0101565 | A1 | 5/2005 | Dasseux et al. | |

FOREIGN PATENT DOCUMENTS

| | | |
|---|---|---|
| WO | WO 96/28553 | 9/1996 |
| WO | WO 97/17434 | 5/1997 |
| WO | WO 01/66135 | 9/2001 |
| WO | WO 2004/022004 | 3/2004 |
| WO | WO 2004/094471 | 11/2004 |
| WO | WO 2004/103310 | 12/2004 |

OTHER PUBLICATIONS

Shanmugan et al, Development and diagnostic and therapeutic strategies for Alzheimer's disease, Research Progress in Alzheimer's Disease and Dementia, vol. 3, Chapter VIII, p. 193-250.*
Shirish V. Patel, Pharmacotherapy of Cognitive Impairment in Alzheimer's Disease: A Review, Journal of Geriatric Psychiatry and Neurology, vol. 8, Apr. 1995, p. 81-95.*
Stancu et al, Dual role of lipoproteins in endothelial cell dysfunction in atherosclerosis, Cell Tissue Res., 2012, DOI: 10.1007/s00441-012-1437-1, p. 1-14.*
Francone, O.L. and Fielding, C.J., "Structure-Function Relationships in Human Lecithin: Cholesterol Acyltransferase Site-Directed Mutagenesis at Serine Residues 181 and 216," *Biochemistry*, vol. 30, No. 42, 10074-10077, 1991.
Goldbourt, U., et al., "Isolated Low HDL Cholesterol as a Risk Factor for Coronary Heart Disease Mortality," *Thromb Vasc. Biol.*, vol. 17, No. 1, 107-113, Jan. 1997.
Gordon, D.J., et al., "High-density Lipoprotein Cholesterol and Coronary Heart Disease in Hypercholesterolemic Men: The Lipid Research Clinics Coronary Primary Prevention Trial," *Circulation*, vol. 74, No. 6, 1217-1225, Dec. 1986.
Gordon, D.J., et al., "High-density Lipoprotein Cholesterol and Cardiovascular Disease: Four Prospective American Studies," *Circulation*, vol. 79, No. 1, 8-15, Jan. 1989.
Gordon, David J. and Rifkind, Basil M., "High-Density Lipoprotein—The Clinical Implications of Recent Studies," *The New England Journal of Medicine*, vol. 321, No. 19, 1311-1316, Nov. 9, 1989.
Hovingh, G. Kees, et al., "Inherited Disorders of HDL Metabolism and Atherosclerosis," *Current Opinion in Lipidology*, vol. 16, 139-145, 2005.
Hovingh, G. Kees, et al., "Compromised LCAT Function is Associated with Increased Atherosclerosis," *Circulation*, vol. 112, 879-884, Aug. 9, 2005.
Jonas, Ana, "Lecithin Cholesterol Acyltransferase," *Biochimica et Biophysica Acta*, 1529: 245-256, 2000.
Karmin, O., et al., "Lecithin: Cholesterol Acyltransferase: Role of N-linked Glycosylation in Enzyme Function," *Biochem J.*, vol. 294, 879-884, 1993.
Krimbou, Larbi, et al., "Interaction of Lecithin: Cholesterol Acyltransferase (LCAT) $\alpha_2$-Macroglobulin Complex with Low Density Lipoprotein Receptor-related Protein (LRP)," *The Journal of Biological Chemistry*, vol. 276, No. 35, 33241-33248, Aug. 31, 2001.
Lee, Richard G., et al., "Plasma Cholesteryl Esters Provided by Lecithin: Cholesterol Acyltransferase and Acyl-Coenzyme A: Cholesterol Acyltransferase 2 Have Opposite Atherosclerotic Potential," *Circulation Research*, vol. 95, 998-1004, Oct. 14, 2004.
McLean, John, et al., "Cloning and Expression of Human Lecithin-Cholesterol Acyltransferase cDNA," *Proc. Natl. Acad. Sci.*, vol. 83, 2335-2339, Apr. 1986.
Peelman, F., et al., "A Proposed Architecture for Lecithin Cholesterol Acyl Transferase (LCAT): Identification of the Catalytic Triad and Molecular Modeling," *Protein Science*, vol. 7, 587-599, 1998.
Peelman, Frank, et al., "Structure and Function of Lecithin Cholesterol Acyl Transferase: New Insights from Structural Predictions and Animal Models," *Current Opinion in Lipidology*, vol. 11, 155-160, 2000.
Wang, K. et al., "Importance of the free sulfhydryl groups of lecithin-cholesterol acyltransferase for its sensitivity to oxidative inactivation," *Biochimica and Biophysica Acta.z*, 1488:268-277, 2000.

* cited by examiner

*Primary Examiner* — Cecilia J Tsang
*Assistant Examiner* — Sergio Coffa
(74) *Attorney, Agent, or Firm* — William L. Leschensky

(57) ABSTRACT

The invention provides compounds, pharmaceutical compositions and methods for treating atherosclerosis, inflammation, thrombosis and other conditions and for decreasing or prevention of accumulation of cholesterol in a subject by modifying LCAT polypeptide.

6 Claims, 7 Drawing Sheets

MGPPGSPWQWVTLLLGLLLPPAAPFWLLNVLFPPHTTPKAELSNHTRPVILVPGCLGNQLEAKLDKPDVVNWMCYRKTED
FFTIWLDLNMFLPLGVDCWIDNTRVVYNRSSGLVSNAPGVQIRVPGFG KTYSVEYLDSSKLAGYLHTLVQNLVNNGYVRD
ETVRAAPYDWRLEPGQQEEYYRKLAGLVEEMHAAYGKPVFLIGHSLGCLHLLYFLLRQPQAWKDRFIDGFISLGAPWGGSIK
PMLVLASGDNQGIPIMSSIKLKEEQRITTTSPWMFPSRMAWPEDHVFISTPSFNYTGRDFQRFFADLHFEEGWYMWLQSRDLL
AGLPAPGVEVYCLYGVGLPT PRTYIYDHG FPYTDPVGVLYEDGDDTVATRSTELCGLWQGRQPQPVHLLPLHGIQHLNM
VFSNLTLEHINAILLGAYRQGPPASPTASPEPPPPE

1B

MGLPGSPWQRVLLLLGLLLPPATPFWLLNVLFPPHTTPKAELSNHTRPVILVPGCLGNRLEAKLDKPDVVNWMCYRKTEDFF
TIWLDFNLFLPLGVDCWIDNTRIVYNHS SGRVSNAPGVQIRVPGFGKTESVEYVDDNKLAGYLHTLVQNLVNNGYVRDETV
RAAPYDWRLAPHQQDEYYKKLAGLVEEMYAAYGKPVFLIGHSLGCLHVLHFLLRQPQSWKDHFIDGFISLGAPWGGSIKAM
RILASGDNQGIPILSNIKLKEEQRITTTSPWMLPAPHVWPEDHVFISTPNFNYTVQDFERFFTDLHFEEGWHMFLQSRDLLERL
PAPGVEVYCLYGGRPTPHTYIYDHNFPYKDPVAALYEDGDDTVATRSTELCGQWQGRQSQPVHLLPMNETDHLNMVFSNKTME
HINAILLGAYRTPKSPAASPSPPPPE

1C mglpgspwqwvllllglllppatsfwllnvlfpphttpkaelsnhtrpvilvpgcmgnrleakldkpnvvnwlcyrktedfftiwldfnm
flplgvdcwidntrvvynrssghmsnapgvqirvpgfgktysveylddnklagylhtlvqnlvnngyvrdetvraapydwrlaprqq
deyyqklaglveemyaaygkpvflighslgclhvlhfllrqpqswkdhfidgfislgapwggsikpmrilasgdnqgipimsn iklre
eqritttspwmfpahhvwpedhvfistpnfnytgqdferffadlhfeegwhmflqsrdllaglpapgvevyclygvgmptahtyiydhn
fpykdpvaalyedgddtvatrstelcgqwqgrqsqavhllpmngtdhlnmvfsnktlehinaillgayrhgtpksptaslgpptke

1D

MG$X_{1}$PGSPWQ$X_{2}$V$X_{3}$LLLGLLLPPA$X_{4}$PFWLLNVLFPPHTTPKAELSNHTRPVILVPGCLGN$X_{5}$LEAKLDKPDVVNWMCYRK
TEDFFTIWLD$X_{6}$N$X_{7}$FLPLGVDCWIDNTR$X_{8}$VYN$X_{9}$SSG$X_{10}$VSNAPGVQIRVPGFGKT$X_{11}$SVEY$X_{12}$D$X_{13}$$X_{14}$KLAGYLHTLVQ
NLVNNGYVRDETVRAAPYDWRL$X_{15}$P$X_{16}$QQ$X_{17}$EYY$X_{18}$KLAGLVEEM$X_{19}$AAYGKPVFLIGHSLGCLH$X_{20}$L$X_{21}$FLLRQPQ$X_{22}$
WKD$X_{23}$FIDGFISLGAPWGGSIK$X_{24}$M$X_{25}$$X_{26}$LASGDNQGIPI$X_{27}$S$X_{28}$IKLKEEQRITTTSPWM$X_{29}$P$X_{30}$$X_{31}$AWPEDHVFISTP$X_{32}$
FNYTG$X_{33}$DF$X_{34}$RFF$X_{35}$DLHFEEGW$X_{36}$M$X_{37}$LQSRDLL$X_{38}$$X_{39}$LPAPGVEVYCLYGVG$X_{40}$PTP$X_{41}$TYIYDH$X_{42}$FPY$X_{43}$DPV$X_{44}$
$X_{45}$LYEDGDDTVATRSTELCG$X_{46}$WQGRQ$X_{47}$QPVHLLP$X_{48}$$X_{49}$$X_{50}$$X_{51}$QHLNMVFSNLT$X_{52}$EHINAILLGAYRQGPP$X_{53}$SP$X_{54}$
ASP$X_{55}$PPPP$X_{56}$ $X_1$ = P, L; $X_2$ = W, R; $X_3$ = T, L; $X_4$ = A, T; $X_5$ = Q, R; $X_6$ = L, F; $X_7$ = M, L; $X_8$ = V, I; $X_9$ = R, H; $X_{10}$ = L, R; $X_{11}$ = Y, E; $X_{12}$ = L, V; $X_{13}$ = S, D; $X_{14}$ = S, N' $X_{15}$ = E, A; $X_{16}$ = Q, H; $X_{17}$ = E, Q; $X_{18}$ = R, K; $X_{19}$ = H, Y; $X_{20}$ = H, L; $X_{21}$ = Y, H; $X_{22}$ = A, S; $X_{23}$ = R, H; $X_{24}$ = P, A; $X_{25}$ = L, R; $X_{26}$ = V, I; $X_{27}$ = M, L; $X_{28}$ = S, N; $X_{29}$ = F, L; $X_{30}$ = R, P; $X_{31}$ = M, H; $X_{32}$ = S, N; $X_{33}$ = R, Q; $X_{34}$ = Q, E; $X_{35}$ = A, T; $X_{36}$ = Y, M; $X_{37}$ = W, F; $X_{38}$ = A, E; $X_{39}$ = G, R; $X_{40}$ = L, R; $X_{41}$ = R, H; $X_{42}$ = G, N; $X_{43}$ = T, K; $X_{44}$ = G, A; $X_{45}$ = V, A; $X_{46}$ = L, Q; $X_{47}$ = P, S; $X_{48}$ = L, M; $X_{49}$ = H, N; $X_{50}$ =G, E; $X_{51}$ = I, T; $X_{52}$ =L, M; $X_{53}$ = A, K; $X_{54}$= T, A; $X_{55}$ = E, S; $X_{56}$ = E, C

2(B)

2(A)

C

B

A

A

B

METHODS FOR TREATING ATHEROSCLEROSIS

CROSS-REFERENCE TO RELATED PATENT APPLICATIONS

This application is a division of U.S. Nonprovisional application Ser. No. 11/823,251, filed Jun. 26, 2007, which claims the benefit of priority of U.S. Provisional Patent Application No. 60/816,415, filed on Jun. 26, 2006, both of which are hereby incorporated by reference.

The present application incorporates by reference in its entirety all subject matter contained in the attached sequence listing which is in txt format is identified by the name of the file, A-1100-US-DIV_Seqlist.txt, created on Apr. 14, 2011, the size of which file is 20 KB.

FIELD OF THE INVENTION

This invention relates generally to the field of medicine and, more specifically, to compositions and methods for treating coronary heart disease and atherosclerosis.

BACKGROUND OF THE INVENTION

Over 50 million Americans have cardiovascular problems, and many other countries face high and increasing rates of cardiovascular disease. It is the number one cause of death and disability in the United States and most European countries. By the time that heart problems are detected, the underlying cause, atherosclerosis, is usually quite advanced, having progressed for decades.

Atherosclerosis is a polygenic complex disease of mammals characterized by the deposits or plaques of lipids and other blood derivatives in the arterial walls (aorta, coronary arteries, carotid). These plaques can be calcified to a greater or lesser extent according to the progression of the process. They are also associated with the accumulation of fatty deposits consisting mainly of cholesterol esters in the arteries. Cholesterol accumulates in the foam cells of the arterial wall, thereby narrowing the lumen and decreasing the flow of blood. This is accompanied by a thickening of the arterial wall, with hypertrophy of the smooth muscle, the appearance of foam cells and the accumulation of the fibrous tissue. Hypercholesterolemia can therefore result in very serious cardiovascular pathologies such as infarction, peripheral vascular disease, stroke, sudden death, cardiac decompensation, cerebral vascular accidents and the like.

The cholesterol is carried in the blood by various lipoproteins including the low-density lipoproteins (LDL) and the high-density lipoproteins (HDL). The LDL is synthesized in the liver and makes it possible to supply the peripheral tissues with cholesterol. In contrast, the HDL captures cholesterol molecules from the peripheral tissues and transports them to the liver where they are converted to bile acids and excreted. The development of atherosclerosis and the risk of coronary heart disease (CHD) inversely correlate to the levels of HDL in the serum. Gordon et al. (1989) N. Engl. J. Med. 321: 1311; Goldbourt et al. (1997) Thromb Vasc. Biol. 17: 107. Low HDL cholesterols often occur in the context of central obesity, diabetes and other features of the metabolic syndrome. Goldbourt et al., supra. It has been suggested that low HDL cholesterol levels are associated with an increased risk of CHD, while high concentrations of HDL have a protective effect against the development of premature atherosclerosis. Gordon et al. (1986) Circulation 74: 1217. Studies demonstrated that the risk for developing clinical atherosclerosis in men drops 3% with a 1% increase in the concentration of HDL in plasma. Gordon et al. (1989) N. Engl. J. Med. 321: 1311. It has been established that concentrations of LDL cholesterol can be reduced by treatment with statins, inhibitors of the cholesterols biosynthesis enzyme 3-hydroxyl-3-methylglutaryl Coenzyme A reductase and thereby this treatment has been used as a successful approach for reducing the risk for atherosclerosis where the primary indication is high LDL level. However, it remains unclear whether statins are beneficial for patients whose primary lipid abnormality is low HDL cholesterol.

Lecithin-cholesterol acyltransferase (LCAT) is an enzyme which catalyzes the esterification of free cholesterol by the transfer of an acyl group from phosphatidylcholine onto 3-hydroxyl group of the cholesterol, forming cholesteryl ester and lysophosphatidylcholine. McLean et al. (1986) Proc. Natl. Acad. Sci. 83: 2335 and McLean et al. (1986) Nucleic Acids Res. 14(23): 9397. LCAT is synthesized in the liver and released into the plasma, where it is combined with HDL, called anti-atherogenic lipoproteins. These HDL particles have the capacity to accept the excess cholesterol, which is then esterified by LCAT. The cholesteryl ester molecules in the HDL particles are either transported to the liver directly through SR-BI receptor, or transferred to apoB-containing lipoproteins, including very low density lipoproteins (VLDL) and LDL, mediated by CETP, and then transported to the liver through LDL-receptor pathway. This mechanism, called reverse cholesterol transport (Glomset (1968) J. Lipid Res. 9:155), allows the removal of excess cholesterol from the body, and therefore is involved in the prevention of atherogenesis. LCAT plays a significant role in this process by creating a gradient of free cholesterol between the plasma membranes and the circulating lipoproteins.

This invention provides compositions comprising LCAT modified to increase enzymatic activity and/or stability and methods for treatment and prevention of atherosclerosis, CHD, and other conditions, including inflammation, thrombosis, and disorders associated with these conditions using the compounds and compositions of the invention.

SUMMARY OF THE INVENTION

The present invention provides methods for treating atherosclerosis in a subject in need thereof comprising administering to the subject a therapeutically effective amount of a compound of Formula I

I

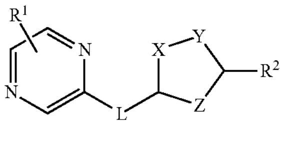

wherein all substituents are as indicated in Detailed Description below, or a pharmaceutically acceptable salts thereof. In one aspect, the invention provides methods for treating atherosclerosis in a subject wherein X and Y are each —N═. In another aspect, Z can be —S—. In a further aspect, L can be —S—. In one aspect, $R^1$ can be CN. In another aspect, $R^2$ can be $SR^3$. In one aspect, $R^3$ can be $C_1$-$C_4$ alkyl, for example, methyl.

In one aspect, the invention provides methods for treating atherosclerosis, inflammation, thrombosis, and conditions associated with these disorders in a subject comprising administering to the subject in need thereof a therapeutically effective amount of a compound selected from the group consisting of 3-(5-(methylthio)-1,3,4-thiadiazol-2-ylthio) pyrazine-2-carbonitrile, 3-(5-(ethylthio)-1,3,4-thiadiazol-2-ylthio)pyrazine-2-carbonitrile, 3-(5-(allylthio)-1,3,4-thiadiazol-2-ylthio)pyrazine-2-carbonitrile, 3-(5-(propylthio)-1,3,4-thiadiazol-2-ylthio)pyrazine-2-carbonitrile, 3-(5-(butylthio)-1,3,4-thiadiazol-2-ylthio)pyrazine-2-carbonitrile, 3-(5-(isobutylthio)-1,3,4-thiadiazol-2-ylthio) pyrazine-2-carbonitrile, 3-(5-(pentylthio)-1,3,4-thiadiazol-2-ylthio)pyrazine-2-carbonitrile, 3-(5-(dodecylthio)-1,3,4-thiadiazol-2-ylthio)pyrazine-2-carbonitrile, 3-(5-(benzylthio)-1,3,4-thiadiazol-2-ylthio)pyrazine-2-carbonitrile, 3-(5-mercapto-1,3,4-thiadiazol-2-ylthio) pyrazine-2-carbonitrile, 3-(5-(isopropylthio)-4-methyl-4H-1,2,4-triazol-3-ylthio)pyrazine-2-carbonitrile, 3-(5-(methylthio)-1,2,4-thiadiazol-3-ylthio)pyrazine-2-carbonitrile, 3-(5-methyl-1,3,4-thiadiazol-2-ylthio)pyrazine-2-carbonitrile, 3-(5-butyl-1,3,4-thiadiazol-2-ylthio) pyrazine-2-carbonitrile, 3-(4-methyl-4H-1,2,4-triazol-3-ylthio)pyrazine-2-carbonitrile, 3-(1-methyl-1H-imidazol-2-ylthio)pyrazine-2-carbonitrile, and 2-chloro-3-(5-(methylthio)-1,3,4-thiadiazol-2-ylthio)pyrazine or a pharmaceutically acceptable salt thereof.

The invention further provides methods for treating atherosclerosis, inflammation, thrombosis, and conditions associated with these disorders in a subject comprising administering to the subject in need thereof a therapeutically effective amount of a modified LCAT comprising a replacement of the amino acid residue 31 by a cysteine residue, wherein the cysteine residue is modified by replacing the thiol hydrogen with 3-pyrazinyl-2-carbonitrile.

In one aspect, the modified LCAT can be administered intravenously, for example, by bolus.

The invention provides methods for treating an LCAT-mediated disease comprising administering to a subject in need thereof an effective amount of a modified LCAT comprising a replacement of the amino acid residue 31 by a cysteine residue, wherein the cysteine residue is modified by replacing the thiol hydrogen with 3-pyrazinyl-2-carbonitrile. In one aspect, the LCAT-mediated disease can be atherosclerosis, thrombosis, coronary heart disease, high blood pressure, LCAT deficiency syndrome, Alzheimer's disease, corneal opacity, metabolic syndrome, dyslipidemia, myocardial infarction, stroke, critical limb ischemia or angina, inflammation, and conditions associated with these disorders.

The invention further provides methods for increasing HDL cholesterol in a subject comprising administering to the subject in need thereof a therapeutically effective amount of a modified LCAT comprising a replacement of the amino acid residue 31 by a cysteine residue, wherein the cysteine residue is modified by replacing the thiol hydrogen with 3-pyrazinyl-2-carbonitrile. In one aspect, the invention provides methods for preventing accumulation of cholesterol in a subject comprising administering to the subject a pharmaceutical composition comprising a therapeutically effective amount of a modified LCAT comprising a replacement of the amino acid residue 31 by a cysteine residue, wherein the cysteine residue is modified by replacing the thiol hydrogen with 3-pyrazinyl-2-carbonitrile, and a pharmaceutically acceptable carrier or excipient.

The invention provides a pharmaceutical composition comprising a modified LCAT comprising a replacement of the amino acid residue 31 by a cysteine residue, wherein the cysteine residue is modified by replacing the thiol hydrogen with 3-pyrazinyl-2-carbonitrile, and a pharmaceutically acceptable carrier.

In one aspect, the subject can be mammalian. In another aspect, the subject can be human.

BRIEF DESCRIPTION OF THE DRAWINGS

FIG. 1 schematically represents sequences of human (A, SEQ ID NO: 1), mouse (B, SEQ ID NO: 2), rat (C, SEQ ID NO: 3), and consensus LCAT polypeptide (D, SEQ ID NO: 4).

DETAILED DESCRIPTION OF THE INVENTION

I. Definitions

Figure 2:
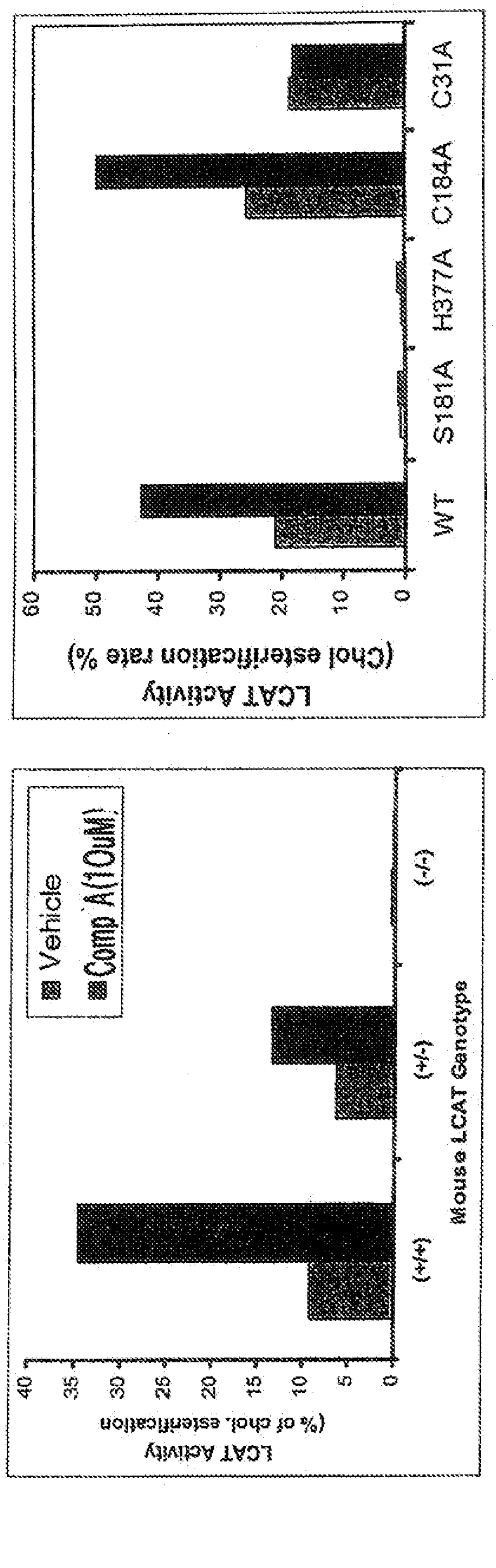
FIG. 2(A) demonstrates activity and specificity of the compounds of the invention on LCAT enzyme.
FIG. 2(B) illustrates the mechanism of action of compounds of the invention on LCAT enzyme.

The term "pharmacologically active" means that a substance so described is determined to have activity that affects a medical parameter or disease state.

"Substantially homogenous" as used herein with reference to an LCAT preparation means that the preparation includes a single species of a therapeutic LCAT compound detectable in the preparation of total therapeutic molecules in the preparation, unless otherwise stated at a specific percentage of total therapeutic molecules. In general, a substantially homogenous preparation is homogenous enough to display the advantages of a homogenous preparation, e.g., ease in clinical application in predictability of lot to lot pharmacokinetics.

"Bioefficacy" refers to the capacity to produce a desired biological effect. Bioefficacy of different compounds, or different dosages of the same compound, or different administrations of the same compound are generally normalized to the amount of compound(s) to permit appropriate comparison.

The term "LCAT" or "lecithin-cholesterol acyltransferase", as used herein, refers to a glycoprotein enzyme that catalyzes the synthesis of cholesterol esters and lysolecithin from phosphatidylcholine and unesterified cholesterol present in lipoproteins. This enzyme is produced primarily by the liver and circulates in blood reversibly bound to lipoproteins. Human LCAT has a polypeptide mass of 49 kDa, or around 67 kDa with added carbohydrate mass. Any polypeptide variants or fragments of mammalian LCAT that have the LCAT enzymatic activity as described above and in more detail below are useful as compounds and in methods of the instant invention. A polypeptide fragment is a stretch of amino acid residues of at least 12 contiguous amino acids from a particular sequence. Some mammalian LCAT sequences for obtaining the modified LCAT useful in this invention are represented in FIG. 1.

The term "modified LCAT," "derivatized LCAT," or "LCAT derivative" refers to lecithin-cholesterol acyltransferase as defined above, with either increased enzymatic activity, wherein the enzymatic activity of the modified LCAT is increased compared to the wild type LCAT as measured in the same assay conditions; or increased plasma stability or half-life time, wherein LCAT stability is improved compared to wild type LCAT plasma stability as measured in the same assay conditions. Assays for measuring LCAT enzyme activity include, e.g., use of apoAI-liposome assay and use of plasma LCAT activity assay, which determine cholesterol esterification rate in an artificial system and in a physiologically relevant system, respectively. Assays for measuring LCAT stability in vivo includes ELISA, which determines the half-life of recombinant LCAT protein in the blood after LCAT protein administration.

"Atherosclerosis" refers to a condition characterized by the hardening and/or narrowing of the arteries caused by the buildup of atheromatous plaque inside the arterial walls. The atheromatous plaque is divided in three components, (1) the atheroma, a nodular accumulation of a soft flaky material at the center of large plaques, composed of macrophages nearest the lumen of the artery; (2) underlying areas of cholesterol crystals; (3) calcification at the outer base of more advanced lesions. Indicators of atherosclerosis include, for example, the development of plaques in the arteries, their calcification, the extent of which can be determined by Sudan IV staining, or the development of foam cells in arteries. The narrowing of the arteries can be determined by coronary angioplasty, ultrafast CT, or ultrasound.

"Inflammation" or "inflammatory disorder" refers to a localized, protective response elicited by injury or destruction of tissues, which serves to destroy, dilute or wall off (sequester) both the injurious agent and the injured tissue. The term "inflammatory disease" or "inflammatory condition" as used herein, means any disease in which an excessive or unregulated inflammatory response leads to excessive inflammatory symptoms, host tissue damage, or loss of tissue function. Additionally, the term "autoimmune disease," as used herein, means any group of disorders in which tissue injury is associated with humoral or cell-mediated responses to the body's own constituents. The term "allergic disease," as used herein, means any symptoms, tissue damage, or loss of tissue function resulting from allergy. The term "arthritic disease," as used herein, means any of a large family of diseases that are characterized by inflammatory lesions of the joints attributable to a variety of etiologies. The term "dermatitis," as used herein, means any of a large family of diseases of the skin that are characterized by inflammation of the skin attributable to a variety of etiologies. The term "transplant rejection," as used herein, means any immune reaction directed against grafted tissue (including organ and cell (e.g., bone marrow)), characterized by a loss of function of the grafted and surrounding tissues, pain, swelling, leukocytosis and thrombocytopenia.

"Thrombosis" and "thrombosis-related disorder" refer to abnormal thrombus formation that causes obstruction of blood vessels and conditions associated with such obstruction. Blood vessels operate under significant shear stresses that are a function of blood flow shear rate. Frequently, there is damage to small blood vessels and capillaries. When these vessels are damaged, hemostasis is triggered to stop the bleeding. Under typical circumstances, such an injury is dealt with through a sequence of events commonly referred to as the "thrombus formation". Thrombus formation is dependent upon platelet adhesion, activation and aggregation and the coagulation cascade that culminates in the conversion of soluble fibrinogen to insoluble fibrin clot. Thrombus formation at site of wound prevents extravasation of blood components. Subsequently, wound healing and clot dissolution occurs and blood vessel integrity and flow is restored.

The term "HDL" refers to the high-density lipoproteins.

The term "LDL", as used herein, means the low-density lipoproteins.

The term "VLDL" refers to the very low density lipoproteins.

The term "treatment" or "treating" includes the administration, to a subject in need, of an amount of a compound of the invention which will inhibit, decrease or reverse development of, for example, a pathological atherosclerosis, inflammatory, or thrombosis-related condition as disclosed herein without limitation. In another aspect, treatment as used herein means the administration, to a subject in need, of an amount of a compound of the invention, which will increase HDL cholesterol levels "Inhibiting," in connection with inhibiting atherosclerosis, is intended to mean preventing, retarding, stabilizing, or reversing formation or growth of atheromatous plaques, inflammatory condition, or thrombosis-related indication. Treatment of diseases and disorders herein is intended to also include therapeutic administration of a compound of the invention (or a pharmaceutical salt, derivative or prodrug thereof) or a pharmaceutical composition containing the compound to a subject (i.e., an animal, for example a mammal, such as a human) believed to be in need of treatment for diseases and disorders, such as, for example, inflammation, thrombosis, coronary heart disease, high blood pressure, LCAT deficiency syndrome, Alzheimer's disease, corneal opacity, metabolic syndrome, dyslipidemia, myocardial infarction, stroke, critical limb ischemia, angina and the like. Treatment also encompasses administration of the compound or pharmaceutical composition to subjects not having been diagnosed as having a need thereof, i.e., prophylactic administration to the subject, such as prevention of accumulation of cholesterol. Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

The phrase "therapeutically effective amount" is the amount of the compound of the invention that will achieve the goal of improvement in disorder severity and the frequency of incidence. The improvement in disorder severity includes, for example, prevention of accumulation of cholesterol in vessel walls increasing of blood levels of HDL cholesterol, the reversal of atherosclerosis, as well as slowing down the progression of atherosclerosis, prevention or treatment of inflammatory disorders, and prevention or treatment of thrombosis-relating conditions.

As used herein, the term "subject" is intended to mean a human or other mammal, exhibiting, or at risk of developing, atherosclerosis, an inflammatory condition or thrombosis. Such an individual can have, or be at risk of developing, for example, atherosclerosis associated with conditions such as thrombosis, coronary heart disease, high blood pressure, LCAT deficiency syndrome, Alzheimer's disease, corneal opacity, metabolic syndrome, dyslipidemia, myocardial infarction, stroke, critical limb ischemia, angina and the like. The prognostic and clinical indications of these conditions are known in the art.

II. LCAT Compounds

The invention provides compounds, pharmaceutical compositions and methods for treating atherosclerosis and for decrease or prevention of accumulation of cholesterol in a subject by modifying LCAT polypeptide. In one aspect, the modified LCAT can be obtained by activation using small molecule compounds of the invention. In another aspect, modified LCAT can be obtained by modification at amino acid residue 31, for example, via the covalent binding to 3-pyrazinyl-2-carbonitrile.

Assays for LCAT activity, plasma stability (enzyme half-life in the plasma) or the plasma LCAT protein levels are known in the art. Absolute LCAT activity in the serum and endogenous cholesterol esterification rate can be determined as described, e.g., in Albers J. et al. (1986) Methods in Enzymol. 129: 763-783; Dobiasova M. et al. (1983) Adv. Lipid Res. 20: 107-194. In one aspect, LCAT activity can be determined by measuring the conversion of radiolabeled cholesterol to cholesterol ester after incubation of LCAT and radiolabeled LCAT substrates containing Apo A-I. Cholesterol esterification rate (nmol CE/mL per hour) can be measured by determining the rate of conversion of labeled cholesterol to cholesteryl ester after incubation of plasma that is radiolabeled with a trace amount of radioactive cholesterol by equilibration with a [$^{14}$C] cholesterol-albumin mixture at 4° C. The endogenous cholesterol esterification rate (as determined with plasma LCAT activity assay) reflects not only on mass of LCAT, but also the nature and amount of LCAT substrate and cofactor present in the serum, and therefore provides a better measure of the therapeutic LCAT activity.

Assays for measuring LCAT stability (half-life) in the blood and plasma LCAT protein concentration are also known in art. After administration, recombinant LCAT protein levels in the plasma can be determined by using ELISA described by J R Crowther (ELISA theory and practice, methods in molecular Biology Volume 42). Reagents for measuring LCAT stability and protein concentration include anti-LCAT antibodies, which are commercially available from several vendors. Examples of use of this assay to determine activity and/or stability of the modified LCAT are given below.

Compounds of the Invention

Generally, reference to a certain element such as hydrogen or H is meant to include all isotopes of that element. For example, if an R group is defined to include hydrogen or H, it also includes deuterium and tritium. Compounds comprising radioisotopes such as tritium, $^{14}$C, $^{32}$P and $^{35}$S are thus within the scope of the invention. Procedures for inserting such labels into the compounds of the invention will be readily apparent to those skilled in the art based on the disclosure herein.

In general, "substituted" as used herein refers to a group, such as those defined below, in which one or more bonds to a hydrogen atom contained therein are replaced by a bond to non-hydrogen or non-carbon atoms such as, but not limited to, a halogen atom such as F, Cl, Br, and I; an oxygen atom in groups such as hydroxyl groups, a nitrogen atom in groups such as amines, amides, alkylamines, dialkylamines, arylamines, alkylarylamines, diarylamines, N-oxides.

Substituents, including alkyl and ring groups, may be either monovalent or polyvalent depending on the context of their usage. For example, if description contained the group $R^1$—$R^2$—$R^3$ and $R^2$ was defined as $C_{1-6}$ alkyl, then the $R^2$ alkyl would be considered polyvalent because it must be bonded to at least $R^1$ and $R^3$. Alternatively, if $R^1$ was defined as $C_{1-6}$ alkyl, then the $R^1$ alkyl would be monovalent (excepting any further substitution language).

In general, "unsubstituted" as used herein with reference to a group, means that the group does not have one or more bonds to a hydrogen or carbon atom contained therein replaced by a bond to non-hydrogen or non-carbon atom, as described above.

In general, "alkyl" as used herein either alone or within other terms such as "haloalkyl", "alkylamino" and "cycloalkyl", refers to linear, branched or cyclic radicals having one to about twelve carbon atoms. "Cycloalkyl" is also used exclusively herein to refer specifically to fully or partially saturated cyclic alkyl radicals. Examples of "alkyl" radicals include methyl, ethyl, n-propyl, isopropyl, n-butyl, isobutyl, sec-butyl, tert-butyl, pentyl, isoamyl, hexyl, cyclopropyl, cyclopentyl, cyclohexyl and the like.

In general, "$C_{a-b}$ alkyl" as used herein refers to an alkyl group comprising from a to b carbon atoms in a branched, cyclical or linear relationship or any combination of the three. The alkyl groups described in this section may also contain double or triple bonds. Examples of $C_{1-8}$ alkyl include, but are not limited to the following:

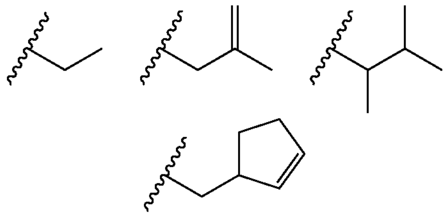

In general, "halogen" and "halo" as used herein, refers to a halogen atoms selected from F, Cl, Br and I.

In general, "haloalkyl", as used herein refers to radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

In general, "$C_{a-b}$ haloalkyl" as used herein refers to an alkyl group, as described above, wherein any number, but at least on of the hydrogen atoms attached to the alkyl chain are replaced by F, Cl, Br or I. Examples of haloalkyl includes, without limitation, trifluoromethyl, pentafluoroethyl and the like.

In general, "heteroalkyl" as used herein refers to an alkyl having one or more of the carbon atoms replaced by a heteroatom, selected from nitrogen, oxygen and sulfur. For example, a heteroalkyl would include an ether or a thioether chain, or an alkoxide moiety, wherein the heteroatom is in the linear region of the moeity. The term also includes moieties where the heteroatom is in a branched region. For example, the term includes 2-amino-n-hexane or 5-hydroxy-pentane.

In general, "hydroxyalkyl" as used herein refers to linear or branched alkyl radicals having one to about ten carbon atoms any one of which may be substituted with one or more hydroxyl radicals. Examples of such radicals include hydroxymethyl, hydroxyethyl, hydroxypropyl, hydroxybutyl and hydroxyhexyl.

In general, "alkoxy" as used herein refers to linear or branched oxy-containing radicals each having alkyl portions of one to about ten carbon atoms. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals. Examples of lower haloalkoxy radicals having one to three carbon atoms include fluoromethoxy, chloromethoxy, trifluoromethoxy, trifluoroethoxy, fluoroethoxy and fluoropropoxy.

In general, "sulfonyl", as used herein whether alone or linked to other terms such as alkylsulfonyl, refers to divalent radicals $—SO_2—$.

In general, "aryl", as used herein alone or in combination, refers to a carbocyclic aromatic system containing one, two or three rings wherein such rings may be attached together in a fused manner. The term "aryl" includes, without limitation, aromatic radicals such as phenyl, naphthyl, indenyl, tetrahydronaphthyl, and indanyl. The "aryl" group may have 1 to 3 substituents such as alkyl, hydroxyl, halo, haloalkyl, nitro, cyano, alkoxy and alkylamino "Aryl" also includes the moiety wherein the aromatic carbocycle is fused with a $C_{3-6}$ cycloalkyl bridge, wherein the bridge optionally includes 1, 2 or 3 heteroatoms selected from N, O and S. For example, phenyl substituted with $—O—CH_2—O—$ forms the aryl benzodioxolyl substituent.

"Saturated or unsaturated" means a substituent that is completely saturated, completely unsaturated, or has any degree of unsaturation in between. Examples of a saturated or unsaturated 6-membered ring carbocycle would include phenyl, cyclohexyl, cyclohexenyl and cyclohexadienyl.

In general, "salt" refers to a salt form of a free base compound of the present invention, as appreciated by persons of ordinary skill in the art. Salts may be prepared by conventional means, known to those skilled in the art. In general, "pharmaceutically-acceptable", when used in reference to a salt, refers to salt forms of a given compound, which are within governmental regulatory safety guidelines for ingestion and/or administration to a subject. The term "pharmaceutically-acceptable salts" embraces salts commonly used to form alkali metal salts and to form addition salts of free acids or free bases. The nature of the salt is not critical, provided that it is pharmaceutically acceptable. Some specific examples are acetate; trifluoroacetate; hydrohalides, such as hydrochloride and hydrobromide; sulfate; citrate; tartrate; glycolate; and oxalate.

Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid.

Suitable pharmaceutically acceptable base addition salts of compounds of Formula I include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine.

Additional examples of such acid and base addition salts can be found in Berge et al., J. Pharm. Sci., 66, 1 (1977). All of these salts may be prepared by conventional means from the corresponding compound of the invention by reacting, for example, the appropriate acid or base with the compound of Formula I.

Also, the basic nitrogen-containing groups of compounds of Formula I can be quaternized with such agents as lower alkyl halides including, without limitation, methyl, ethyl, propyl, and butyl chloride, bromides and iodides; dialkyl sulfates including dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products may be obtained by quaternizing such basic nitrogen groups in compounds of Formula I.

In general, "derivative" as used herein, refers to simple modifications, readily apparent to those of ordinary skill in the art, on the parent core structure of Formula I, which does not significantly affect (generally decrease) the activity of the compound in-vitro as well as in vivo, in a subject. The term, "derivative" as used herein, is contemplated to include pharmaceutically acceptable derivatives of compounds of Formula I.

In general, "leaving group" as used herein, refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Exemplary leaving groups are indicated herein where appropriate.

In general, "protecting group" as used herein, refers to groups well known in the art which are used to prevent selected reactive groups, such as carboxy, amino, hydroxy, mercapto and the like, from undergoing undesired reactions, such as nucleophilic, electrophilic, oxidation, reduction and the like. Protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, for example those having 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, tri-chloro acetyl, phthaloyl and the like. A mixture of protecting groups can be used to protect the same amino group, such as a primary amino group can be protected by both an aralkyl group and an aralkoxycarbonyl group Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl Amino groups may also be protected against undesired reactions, such as oxidation, through the formation of an addition salt, such as hydrochloride, toluenesulfonic acid, trifluoroacetic acid and the like. Many of the amino protecting groups, including aralkyl groups for example, are also suitable for protecting carboxy, hydroxy and mercapto groups. Alkyl groups are also suitable groups for protecting hydroxy and mercapto groups, such as tert-butyl.

Silyl protecting groups are groups containing silicon atoms which are optionally substituted by one or more alkyl, aryl and aralkyl groups. Suitable silyl protecting groups include, but are not limited to, trimethylsilyl, triethylsilyl, tri-isopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-tri-silyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. One method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'═O, S, NR), and the like, which are illustrated in the following examples:

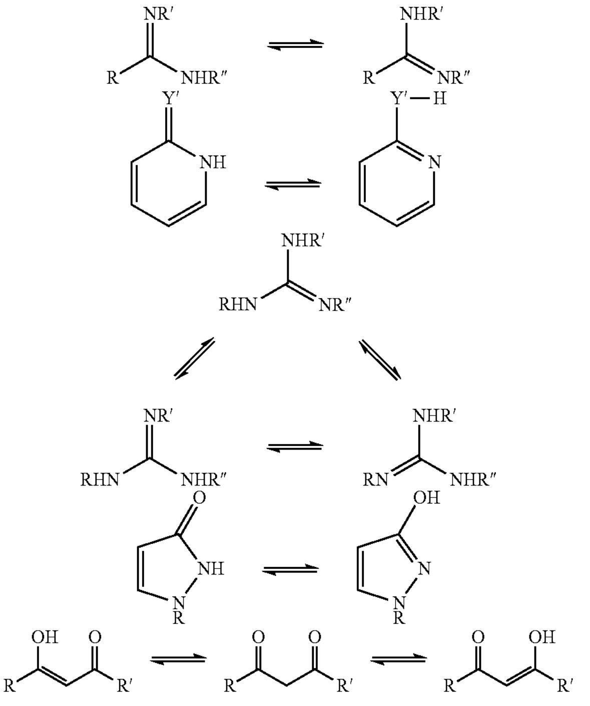

and though one form is named, described, displayed and/or claimed herein, all the tautomeric forms are intended to be inherently included in such name, description, display and/or claim.

A. Derivatives

In addition to LCAT modifications described above, it is contemplated that other “derivatives” of LCAT may be substituted for an LCAT protein described above. Such derivatives may improve the solubility, absorption, biological half life, and the like of the compounds. The moieties may alternatively eliminate or attenuate any undesirable side-effect of the compounds and the like.

Such derivative LCATs include compounds in which:

1. The compound or some portion thereof is cyclic. For example, the peptide portion may be modified to contain two or more cysteine residues (e.g., in the linker), which could cyclize by disulfide bond formation.

2. The compound is cross-linked or is rendered capable of cross-linking between molecules. For example, the peptide portion may be modified to contain one cysteine residue and thereby be able to form an intermolecular disulfide bond with a like molecule. The compound may also be cross-linked through its C-terminus.

3. One or more peptidyl [—C(O)NR—] linkages (bonds) is replaced by a non-peptidyl linkage. Exemplary non-peptidyl linkages are —$CH_2$-carbamate [—$CH_2$—OC(O)NR—], phosphonate, —$CH_2$-sulfonamide [—$CH_2$—$S(O)_2$NR—], urea [—NHC(O)NH—], —$CH_2$-secondary amine, and alkylated peptide [—C(O)$NR_6$— wherein $R_6$ is lower alkyl].

4. The N-terminus is derivatized. Typically, the N-terminus may be acylated or modified to a substituted amine Exemplary N-terminal derivative groups include —NRR1 (other than —$NH_2$), —NRC(O)R1, —NRC(O)OR1, —$NRS(O)_2$ R1, —NHC(O)NHR1, succinimide, or benzyloxycarbonyl-NH— (CBZ-NH—), wherein R and R1 are each independently hydrogen or lower alkyl with the proviso that R and R1 are not both hydrogen and wherein the phenyl ring may be substituted with 1 to 3 substituents selected from the group consisting of C1-C4 alkyl, C1-C4 alkoxy, chloro, and bromo; to a succinimide group; to a benzyloxycarbonyl-NH— (CBZ-NH—) group; and peptides wherein the free C terminus is derivatized to —C(O)R2 where R2 is selected from the group consisting of lower alkoxy and —NR3R4 where R3 and R4 are independently selected from the group consisting of hydrogen and lower alkyl. By "lower" is meant a group having from 1 to 6 carbon atoms.

5. The free C-terminus is derivatized. Typically, the C-terminus is esterified or amidated. For example, one may use methods described in the art to add (NH—CH2-CH2-NH2)2 to compounds of this invention at the C-terminus Likewise, one may use methods described in the art to add —NH2 to compounds of this invention at the C-terminus Exemplary C-terminal derivative groups include, for example, —C(O) R2 wherein R2 is lower alkoxy or —NR3R4 wherein R3 and R4 are independently hydrogen or C1-C8 alkyl (preferably C1-C4 alkyl).

6. A disulfide bond is replaced with another, preferably more stable, cross-linking moiety (e.g., an alkylene). See, e.g., Bhatnagar et al. (1996), J. Med. Chem. 39: 3814-9; Alberts et al. (1993) Thirteenth Am. Pep. Symp., 357-9.

7. One or more individual amino acid residues is modified. Various derivatizing agents are known to react specifically with selected side chains or terminal residues, as described in detail below.

Additionally, modifications of individual amino acids may be introduced into the LCAT amino acid sequence by reacting targeted amino acid residues of the protein with an organic derivatizing agent that is capable of reacting with selected side chains or terminal residues. The following are exemplary.

Lysinyl and amino terminal residues may be reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine guanidino group.

The specific modification of tyrosyl residues per se has been studied extensively, with particular interest in introducing spectral labels into tyrosyl residues by reaction with aromatic diazonium compounds or tetranitromethane. Most commonly, N-acetylimidazole and tetranitromethane may be used to form O-acetyl tyrosyl species and 3-nitro derivatives, respectively.

Carboxyl side groups (aspartyl or glutamyl) may be selectively modified by reaction with carbodiimides (R'—N═C═N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues may be converted to asparaginyl and glutaminyl residues by reaction with ammonium ions.

Glutaminyl and asparaginyl residues are frequently deamidated to the corresponding glutamyl and aspartyl residues. Alternatively, these residues may be deamidated under mildly acidic conditions. Either form of these residues falls within the scope of this invention.

Cysteinyl residues at a position other than residue 31 can be replaced by amino acid residues or other moieties either to eliminate disulfide bonding or, conversely, to stabilize cross-linking. See, e.g., Bhatnagar et al. (1996), J. Med. Chem. 39: 3814-9.

Derivatization with bifunctional agents is useful for cross-linking the peptides or their functional derivatives to a water-insoluble support matrix or to other macromolecular carriers. Commonly used cross-linking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 may be employed for protein immobilization.

Other possible modifications include hydroxylation of proline and lysine, phosphorylation of hydroxyl groups of seryl or threonyl residues, oxidation of the sulfur atom in cysteine, methylation of the alpha-amino groups of lysine, arginine, and histidine side chains (Creighton, T. E., Proteins: Structure and Molecule Properties, W.H. Freeman & Co., San Francisco, pp. 79-86 (1983)), acetylation of the N-terminal amine, and, in some instances, amidation of the C-terminal carboxyl groups.

Such derivatized moieties preferably improve one or more characteristics including thrombopoietic activity, solubility, absorption, biological half life, and the like of the inventive compounds. Alternatively, derivatized moieties result in compounds that have the same, or essentially the same, characteristics and/or properties of the compound that is not derivatized. The moieties may alternatively eliminate or attenuate any undesirable side effect of the compounds and the like.

Carbohydrate (oligosaccharide) groups may conveniently be attached to sites that are known to be glycosylation sites in proteins. Generally, O-linked oligosaccharides are attached to serine (Ser) or threonine (Thr) residues while N-linked oligosaccharides are attached to asparagine (Asn) residues when they are part of the sequence Asn-X-Ser/Thr, where X can be any amino acid except proline. X is preferably one of the 19 naturally occurring amino acids other than proline. The structures of N-linked and O-linked oligosaccharides and the sugar residues found in each type are different. One type of sugar that is commonly found on both is N-acetylneuraminic acid (referred to as sialic acid). Sialic acid is usually the terminal residue of both N-linked and O-linked oligosaccharides and, by virtue of its negative charge, may confer acidic properties to the glycosylated compound. Such site(s) may be incorporated in the linker of the compounds of this invention and are preferably glycosylated by a cell during recombinant production of the polypeptide compounds (e.g., in mammalian cells such as CHO, BHK, COS). However, such sites may further be glycosylated by synthetic or semi-synthetic procedures known in the art.

Compounds of the present invention may be changed at the DNA level, as well. The DNA sequence of any portion of the compound may be changed to codons more compatible with the chosen host cell. For *E. coli*, which is the host cell in one aspect, optimized codons are known in the art. Codons may be substituted to eliminate restriction sites or to include silent restriction sites, which may aid in processing of the DNA in the selected host cell. The vehicle, linker and peptide DNA sequences may be modified to include any of the foregoing sequence changes.

Isotope- and toxin-conjugated derivatives. Another set of useful derivatives are the above-described molecules conjugated to toxins, tracers, or radioisotopes. Such conjugation is especially useful for molecules comprising peptide sequences that bind to tumor cells or pathogens. Such molecules may be used as therapeutic agents or as an aid to surgery (e.g., radioimmunoguided surgery or RIGS) or as diagnostic agents (e.g., radioimmunodiagnostics or RID).

As therapeutic agents, these conjugated derivatives possess a number of advantages. They facilitate use of toxins and radioisotopes that would be toxic if administered without the specific binding provided by the peptide sequence. They also can reduce the side-effects that attend the use of radiation and chemotherapy by facilitating lower effective doses of the conjugation partner.

Useful conjugation partners include:

radioisotopes, such as $^{90}$Yttrium, $^{131}$Iodine, $^{225}$Actinium, and $^{213}$Bismuth;

ricin A toxin, microbially derived toxins such as *Pseudomonas* endotoxin (e.g., PE38, PE40), and the like;

partner molecules in capture systems (see below);

biotin, streptavidin (useful as either partner molecules in capture systems or as tracers, especially for diagnostic use); and cytotoxic agents (e.g., doxorubicin).

One useful adaptation of these conjugated derivatives is use in a capture system. In such a system, the molecule of the present invention would comprise a benign capture molecule. This capture molecule would be able to specifically bind to a separate effector molecule comprising, for example, a toxin or radioisotope. Both the vehicle-conjugated molecule and the effector molecule would be administered to the patient. In such a system, the effector molecule would have a short half-life except when bound to the vehicle-conjugated capture molecule, thus minimizing any toxic side-effects. The vehicle-conjugated molecule would have a relatively long half-life but would be benign and non-toxic. The specific binding portions of both molecules can be part of a known specific binding pair (e.g., biotin, streptavidin) or can result from peptide generation methods such as those described herein.

Such conjugated derivatives may be prepared by methods known in the art. In the case of protein effector molecules (e.g. *Pseudomonas* endotoxin), such molecules can be expressed as fusion proteins from correlative DNA constructs. Radioisotope conjugated derivatives may be prepared, for example, as described for the BEXA antibody (Coulter). Derivatives comprising cytotoxic agents or microbial toxins may be prepared, for example, as described for the BR96 antibody (Bristol-Myers Squibb). Molecules employed in capture systems may be prepared, for example, as described by the patents, patent applications, and publications from NeoRx. Molecules employed for RIGS and RID may be prepared, for example, by the patents, patent applications, and publications from NeoProbe.

The compounds of the invention may also be covalently or noncovalently associated with a carrier molecule, such as a linear polymer (e.g., polyethylene glycol, polylysine, dextran, etc.), a branched-chain polymer (see, for example, U.S. Pat. No. 4,289,872 to Denkenwalter et al., issued Sep. 15, 1981; U.S. Pat. No. 5,229,490 to Tam, issued Jul. 20, 1993; WO 93/21259 by Frechet et al., published 28 Oct. 1993); a lipid; a cholesterol group (such as a steroid); or a carbohydrate or oligosaccharide. Other possible carriers include one or more water soluble polymer attachments such as polyoxyethylene glycol, or polypropylene glycol as described U.S. Pat. Nos. 4,640,835, 4,496,689, 4,301,144, 4,670,417, 4,791,192 and 4,179,337. Still other useful polymers known in the art include monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide copolymer, polyoxyethylated polyols (e.g., glycerol) and polyvinyl alcohol, as well as mixtures of these polymers.

In one aspect, the carrier is polyethylene glycol (PEG). The PEG group may be of any convenient molecular weight and may be straight chain or branched. The average molecular weight of the PEG will range from about 2 kDa to about 100 kDa, or from about 5 kDa to about 50 kDa, or from about 5 kDa to about 10 kDa.

The PEG groups will generally be attached to the compounds of the invention via acylation, reductive alkylation, Michael addition, thiol alkylation or other chemoselective conjugation/ligation methods through a reactive group on the PEG moiety (e.g., an aldehyde, amino, ester, thiol, α-haloacetyl, maleimido or hydrazino group) to a reactive group on the target compound (e.g., an aldehyde, amino, ester, thiol, α-haloacetyl, maleimido or hydrazino group).

Prodrugs of the compounds of this invention are also contemplated by this invention. A "prodrug" is a compound, which when administered to the body of a subject (such as a mammal), breaks down in the subject's metabolic pathway to provide an active compound of Formula I. More specifically, a prodrug is an active or inactive "masked" compound that is modified chemically through in vivo physiological action, such as hydrolysis, metabolism and the like, into a compound of this invention following administration of the prodrug to a subject or patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985).

One common form of a prodrug is a masked carboxylic acid group. Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl) Amines have been masked as arylcarbonyloxymethyl substituted derivatives which are cleaved by esterases in vivo releasing the free drug and formaldehyde (Bundgaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

In general, "stereoisomer" as used herein refers to a compound having one or more asymmetric centers. Chiral centers in a compound generally cause that compound to exist in many different conformations or stereoisomers. The term "stereoisomers" includes enantiomers, diastereomers, atropisomers and geometric isomers. Stereoisomers generally possess different chemical properties and/or biological activity, as appreciated by those skilled in the art. For example, one stereoisomer may be more active and/or may exhibit beneficial effects in comparison to other stereoisomer(s) or when separated from the other stereoisomer(s). However, it is well within the skill of the ordinary artisan to separate, and/or to selectively prepare said stereoisomers. Accordingly, "stereoisomers" of the present invention necessarily include mixtures of stereoisomers, including racemic mixtures, individual stereoisomers, and optically active forms.

In general, "solvate" when used with reference to a compound refers to a compound, which is associated with one or more molecules of a solvent, such as an organic solvent, inorganic solvent, aqueous solvent or mixtures thereof. The compounds of Formula I may also be solvated, especially hydrated. Hydration may occur during manufacturing of the compounds or compositions comprising the compounds, or the hydration may occur over time due to the hygroscopic nature of the compounds. Compounds of the invention may exist as organic solvates as well, including DMF, ether, and alcohol solvates among others. The identification and preparation of any particular solvate is within the skill of the ordinary artisan of synthetic organic or medicinal chemistry.

B. Vehicles

1. Immunoglobulin Constant Region Vehicles

In one aspect, an LCAT protein of the invention includes at least one vehicle attached to the protein through the N-terminus, C-terminus or a side chain of one of the amino acid residues. In one embodiment, an Fc domain is a vehicle. Thus, an Fc domain may be fused to the N or C termini of the peptides or at both the N and C termini. Multiple vehicles, as exemplified herein, may also be used; e.g., Fc's at each terminus or an Fc at a terminus and a PEG group at the other terminus or a side chain.

In various embodiments, the Fc component is either a native Fc or an Fc variant. By way of example and without limitation, the Fc component is an Fc region of the human immunoglobulin IgG1 heavy chain or a biologically active fragment, derivative, or dimer thereof, see Ellison, J. W. et al., Nucleic Acids Res. 10:4071-4079 (1982). It is understood, however, that an Fc region for use in the invention may be derived from an IgG, IgA, IgM, IgE or IgD from any species. Native Fc domains are made up of monomeric polypeptides that may be linked into dimeric or multimeric forms by covalent (i.e., disulfide bonds) and/or non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgGA2). One example of a native Fc is a disulfide-bonded dimer resulting from papain digestion of an IgG (see Ellison et al. (1982), Nucleic Acids Res. 10: 4071-9).

In various aspects, Fc sequence contemplated include those known in the art such as, for example, Fc IgG1 (GenBank Accession No. P01857), Fc IgG2 (GenBank Accession No. P01859), Fc IgG3 (GenBank Accession No. P01860), Fc IgG4 (GenBank Accession No. P01861), Fc IgA1 (GenBank Accession No. P01876), Fc IgA2 (GenBank Accession No. P01877), Fc IgD (GenBank Accession No. P01880), Fc IgM (GenBank Accession No. P01871), and Fc IgE (GenBank Accession No. P01854).

Variants, analogs or derivatives of the Fc portion may be constructed by, for example, making various substitutions of residues or sequences. In one aspect, an Fc variant is incorporated which comprises a molecule or sequence that is humanized from a non-human native Fc. Alternately, an Fc variant comprises a molecule or sequence that lacks one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC), each of which is described in detail in U.S. Patent Application No. 20040087778, the disclosure of which is incorporated by reference in its entirety.

Variant (or analog) polypeptides include insertion variants, wherein one or more amino acid residues supplement an Fc amino acid sequence. Insertions may be located at either or both termini of the protein, or may be positioned within internal regions of the Fc amino acid sequence. Insertion variants, with additional residues at either or both termini, can include for example, fusion proteins and proteins including amino acid tags or labels. For example, the Fc molecule may optionally contain an N-terminal Met, especially when the molecule is expressed recombinantly in a bacterial cell such as *E. coli*.

In Fc deletion variants, one or more amino acid residues in an Fc polypeptide are removed. Deletions can be effected at one or both termini of the Fc polypeptide, or with removal of one or more residues within the Fc amino acid sequence. Deletion variants, therefore, include all fragments of an Fc polypeptide sequence.

In Fc substitution variants, one or more amino acid residues of an Fc polypeptide are removed and replaced with alternative residues. In one aspect, the substitutions are conservative in nature and conservative substitutions of this type are well known in the art. Alternatively, the invention embraces substitutions that are also non-conservative.

For example, cysteine residues can be deleted or replaced with other amino acids to prevent formation of some or all disulfide crosslinks of the Fc sequences. Each cysteine residue can be removed and/or substituted with other amino acids, such as Ala or Ser. As another example, modifications may also be made to introduce amino acid substitutions to (1) ablate the Fc receptor binding site; (2) ablate the complement (Clq) binding site; and/or to (3) ablate the antibody dependent cell-mediated cytotoxicity (ADCC) site. Such sites are known in the art, and any known substitutions are within the scope of Fc as used herein. For example, see Molecular Immunology, Vol. 29, No. 5, 633-639 (1992) with regard to ADCC sites in IgG 1.

Likewise, one or more tyrosine residues can be replaced by phenylalanine residues. In addition, other variant amino acid insertions, deletions and/or substitutions are also contemplated and are within the scope of the present invention. Conservative amino acid substitutions will generally be preferred. Furthermore, alterations may be in the form of altered amino acids, such as peptidomimetics or D-amino acids.

As noted above, both native Fcs and Fc variants are suitable Fc domains for use within the scope of this invention. A native Fc may be extensively modified to form an Fc variant provided binding to the salvage receptor is maintained; see, for example WO 97/34631 and WO 96/32478. In such Fc variants, one may remove one or more sites of a native Fc that provide structural features or functional activity not required by the fusion molecules of this invention. One may remove these sites by, for example, substituting or deleting residues, inserting residues into the site, or truncating portions containing the site. The inserted or substituted residues may also be altered amino acids, such as peptidomimetics or D-amino acids. Fc variants may be desirable for a number of reasons, several of which are described below. Exemplary Fc variants include molecules and sequences in which:

1. Sites involved in disulfide bond formation are removed. Such removal may avoid reaction with other cysteine-containing proteins present in the host cell used to produce the molecules of the invention. For this purpose, the cysteine-containing segment at the N-terminus may be truncated or cysteine residues may be deleted or substituted with other amino acids (e.g., alanyl, seryl). In particular, one may truncate the N-terminal 20-amino acid segment of SEQ ID NO: 3 or delete or substitute the cysteine residues at positions 7 and 10 of SEQ ID NO: 3. Even when cysteine residues are removed, the single chain Fc domains can still form a dimeric Fc domain that is held together non-covalently.

2. A native Fc is modified to make it more compatible with a selected host cell. For example, one may remove the PA sequence near the N-terminus of a typical native Fc, which may be recognized by a digestive enzyme in *E. coli* such as proline aminopeptidase. One may also add an N-terminal methionine residue, especially when the molecule is expressed recombinantly in a bacterial cell such as *E. coli*. The Fc domain of SEQ ID NO: 3 is one such Fc variant.

3. A portion of the N-terminus of a native Fc is removed to prevent N-terminal heterogeneity when expressed in a selected host cell. For this purpose, one may delete any of the first 20 amino acid residues at the N-terminus, particularly those at positions 1, 2, 3, 4 and 5.

4. One or more glycosylation sites are removed. Residues that are typically glycosylated (e.g., asparagine) may confer cytolytic response. Such residues may be deleted or substituted with unglycosylated residues (e.g., alanine).

5. Sites involved in interaction with complement, such as the Clq binding site, are removed. For example, one may delete or substitute the EKK sequence of human IgG 1. Complement recruitment may not be advantageous for the molecules of this invention and so may be avoided with such an Fc variant.

6. Sites are removed that affect binding to Fc receptors other than a salvage receptor. A native Fc may have sites for interaction with certain white blood cells that are not required for the fusion molecules of the present invention and so may be removed.

7. The ADCC site is removed. ADCC sites are known in the art; see, for example, *Molec. Immunol.* 29 (5): 633-9 (1992) with regard to ADCC sites in IgG1. These sites, as well, are not required for the fusion molecules of the present invention and so may be removed.

8. When the native Fc is derived from a non-human antibody, the native Fc may be humanized. Typically, to humanize a native Fc, one will substitute selected residues in the non-human native Fc with residues that are normally found in human native Fc. Techniques for antibody humanization are well known in the art.

It should be noted that Fc monomers will spontaneously dimerize when the appropriate cysteine residues are present, unless particular conditions are present that prevent dimerization through disulfide bond formation. Even if the cysteine residues that normally form disulfide bonds in the Fc dimer are removed or replaced by other residues, the monomeric chains will generally form a dimer through non-covalent interactions. The term "Fc" herein is used to mean any of these forms: the native monomer, the native dimer (disulfide bond linked), modified dimers (disulfide and/or non-covalently linked), and modified monomers (i.e., derivatives).

Fc sequences may also be derivatized, i.e., bearing modifications other than insertion, deletion, or substitution of amino acid residues. In one aspect, the modifications are covalent in nature, and include for example, chemical bonding with polymers, lipids, other organic, and inorganic moieties. However, non-covalent modifications are also contemplated. Derivatives of the invention may be prepared to increase circulating half-life, or may be designed to improve targeting capacity for the polypeptide to desired cells, tissues, or organs.

It is also possible to use the salvage receptor binding domain of the intact Fc molecule as the Fc part of a compound of the invention, such as described in WO 96/32478, entitled "Altered Polypeptides with Increased Half-Life." Additional members of the class of molecules designated as Fc herein are those that are described in WO 97/34631, entitled "Immunoglobulin-Like Domains with Increased Half-Lives." Both of the published PCT applications cited in this paragraph are hereby incorporated by reference.

As discussed herein, the Fc fusions may be at the N or C terminus of a TMP of the invention, or at both the N and C termini of the TMP. It has been previously been shown that peptides in which an Fc moiety is ligated to the N terminus of the TMP group is more bioactive than the other possibilities. When the Fc is fused at the N-terminus of the TMP or linker, such fusion will generally occur at the C-terminus of the Fc chain, and vice versa.

2. Water-soluble polymer vehicles

As noted above, polymer vehicles are also contemplated. Various means for attaching chemical moieties useful as vehicles are currently available, see, e.g., Patent Cooperation Treaty ("PCT") International Publication No. WO 96/11953, entitled "N-Terminally Chemically Modified Protein Compositions and Methods," herein incorporated by reference in its entirety. This PCT publication discloses, among other things, the selective attachment of water soluble polymers to the N-terminus of proteins.

Thus, the invention contemplates compounds comprising a water-soluble polymer (WSP). Suitable, clinically acceptable, WSP include without limitation, PEG, polyethylene glycol propionaldehyde, copolymers of ethylene glycol/propylene glycol, monomethoxy-polyethylene glycol, carboxymethylcellulose, polyacetals, polyvinyl alcohol (PVA), polyvinyl pyrrolidone, poly-1,3-dioxolane, poly-1,3,6-trioxane, ethylene/maleic anhydride copolymer, poly (.beta.-amino acids) (either homopolymers or random copolymers), poly(n-vinyl pyrrolidone)polyethylene glycol, propropylene glycol homopolymers (PPG) and other polyalkylene oxides, polypropylene oxide/ethylene oxide copolymers, polyoxyethylated polyols (POG) (e.g., glycerol) and other polyoxyethylated polyols, polyoxyethylated sorbitol, or polyoxyethylated glucose, colonic acids or other carbohydrate polymers, Ficoll or dextran and mixtures thereof. In fact, any of the forms of PEG that have been used to derivatize other proteins, such as and without limitation mono-(C1-C10) alkoxy- or aryloxy-polyethylene glycol, are provided. Polyethylene glycol propionaldehyde may have advantages in manufacturing due to its stability in water.

The PEG group may be of any convenient molecular weight and may be linear or branched. The average molecular weight of PEG contemplated for use in the invention ranges from about 2 kDa to about 100 kDa, from about 5 kDa to about 50 kDa, from about 5 kDa to about 10 kDa. In another aspect, the PEG moiety has a molecular weight from about 6 kDa to about 25 kDa. PEG groups generally are attached to peptides or proteins via acylation or reductive alkylation through a reactive group on the PEG moiety (e.g., an aldehyde, amino, thiol, or ester group) to a reactive group on the target peptide or protein (e.g., an aldehyde, amino, or ester group). Using methods described herein, a mixture of polymer/peptide conjugate molecules can be prepared, and the advantage provided herein is the ability to select the proportion of polymer/peptide conjugate to include in the mixture. Thus, if desired, a mixture of peptides with various numbers of polymer moieties attached (i.e., zero, one or two) can be prepared with a predetermined proportion of polymer/protein conjugate.

A useful strategy for the PEGylation of synthetic peptides consists of combining, through forming a conjugate linkage in solution, a peptide and a WSP (PEG) moiety, each bearing a special functionality that is mutually reactive toward the other. The peptides can be easily prepared with conventional solid phase synthesis. The peptides are "preactivated" with an appropriate functional group at a specific site. The precursors are purified and fully characterized prior to reacting with the PEG moiety. Ligation of the peptide with PEG usually takes place in aqueous phase and can be easily monitored by reverse phase analytical HPLC. The PEGylated peptides can be easily purified by preparative HPLC and characterized by analytical HPLC, amino acid analysis and laser desorption mass spectrometry.

Polysaccharide polymers are another type of WSP which may be used for protein modification. Dextrans are polysaccharide polymers comprised of individual subunits of glucose predominantly linked by α1-6 linkages. The dextran itself is available in many molecular weight ranges, and is readily available in molecular weights from about 1 kD to about 70 kD. Dextran is a suitable water soluble polymer for use in the present invention as a vehicle by itself or in combination with another vehicle (e.g., Fc). See, for example, WO 96/11953 and WO 96/05309. The use of dextran conjugated to therapeutic or diagnostic immunoglobulins has been reported; see, for example, European Patent Publication No. 0 315 456, which is hereby incorporated by reference. Dextran of about 1 kD to about 20 kD is preferred when dextran is used as a vehicle in accordance with the present invention.

The WSP moiety of the molecule may be branched or unbranched. For therapeutic use of the end-product preparation, the polymer is pharmaceutically acceptable. In general, a desired polymer is selected based on such considerations as whether the polymer conjugate will be used therapeutically, and if so, the desired dosage, circulation time, resistance to proteolysis, and other considerations. In various aspects, the average molecular weight of each WSP is between about 2 kDa and about 100 kDa, between about 5 kDa and about 50 kDa, between about 12 kDa and about 40 kDa and between about 20 kDa and about 35 kDa. In yet another aspect the molecular weight of each polymer is between about 6 kDa and about 25 kDa. The term "about" as used herein and throughout, indicates that in preparations of a water soluble polymer, some molecules will weigh more, some less, than the stated molecular weight. Generally, the higher the molecular weight or the more branches, the higher the polymer/protein ratio. Other sizes may be used, depending on the desired therapeutic profile including for example, the duration of sustained release; the effects, if any, on biological activity; the ease in handling; the degree or lack of antigenicity and other known effects of a water soluble polymer on a therapeutic protein.

The WSP should be attached to the protein with consideration given to effects on functional or antigenic domains of the peptide or protein. In general, chemical derivatization may be performed under any suitable condition used to react a protein with an activated polymer molecule. Activating groups which can be used to link the water soluble polymer to one or more proteins include without limitation sulfone, maleimide, sulfhydryl, thiol, triflate, tresylate, azidirine, oxirane and 5-pyridyl. If attached to the peptide by reductive alkylation, the polymer selected should have a single reactive aldehyde so that the degree of polymerization is controlled.

3. Alternative Vehicles

Alternative vehicles include a protein, polypeptide, peptide, antibody, antibody fragment, or small molecule (e.g., a peptidomimetic compound) capable of binding to a salvage receptor. For example, one could use as a vehicle a polypeptide as described in U.S. Pat. No. 5,739,277, issued Apr. 14, 1998 to Presta et al. Peptides could also be selected by phage display for binding to the FcRn salvage receptor. Such salvage receptor-binding compounds are also included within the meaning of "vehicle" and are within the scope of this invention. Such vehicles should be selected for increased half-life (e.g., by avoiding sequences recognized by proteases) and decreased immunogenicity (e.g., by favoring non-immunogenic sequences, as discovered in antibody humanization).

Compounds that are useful in the methods of the instant invention are, for example, compounds of Formula I

I

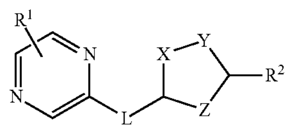

or a stereomer, a tautomer, a solvate, a pharmaceutically acceptable salt, or a prodrug thereof, wherein X, Y and Z are independently selected from the group consisting of —N═, —S—, —CH═ and

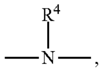

provided that at least two of X, Y and Z are not —S—, and provided that no more than one of X, Y and Z is —CH═; L is —S—, —S(O)—, or —S(O)$_2$—;

$R^1$ is selected from the group consisting of CN, $COOR^5$, $SO_2R^6$ and halogen;

$R^2$ is selected from the group consisting of H, optionally substituted $C_1$-$C_{12}$ alkyl, optionally substituted $C_1$-$C_{12}$ alkenyl, optionally substituted $C_1$-$C_8$ alkynyl, optionally substituted aryl, and optionally substituted heteroaryl, and $SR^3$, wherein the substituents are selected from the group consisting of $C_1$-$C_4$ alkyl, $NH_2$, halo and CN; and wherein $R^3$ is selected from the group consisting of H, optionally substituted $C_1$-$C_{12}$ alkyl, optionally substituted $C_1$-$C_8$ alkenyl, optionally substituted $C_1$-$C_8$ alkynyl, optionally substituted aryl and optionally substituted heteroaryl, wherein the substituents are selected from the group consisting of $NH_2$, halo and CN;

$R^4$ is H or $C_1$-$C_8$ alkyl;

$R^5$ and $R^6$ are each independently $C_1$-$C_4$ alkyl.

In one aspect, X and Y are each —N═.

In another aspect, Z is —S —.

In a further aspect, L is —S —.

In one aspect, $R^1$ is CN.

In another aspect, $R^2$ is $SR^3$. $R^3$ can be $C_1$-$C_4$ alkyl, for example, methyl.

In one aspect, the invention contemplates the use of the following compounds:

3-(5-(Methylthio)-1,3,4-thiadiazol-2-ylthio)pyrazine-2-carbonitrile;

3-(5-(Ethylthio)-1,3,4-thiadiazol-2-ylthio)pyrazine-2-carbonitrile;

3-(5-(Allylthio)-1,3,4-thiadiazol-2-ylthio)pyrazine-2-carbonitrile;

3-(5-(Propylthio)-1,3,4-thiadiazol-2-ylthio)pyrazine-2-carbonitrile;

3-(5-(Butylthio)-1,3,4-thiadiazol-2-ylthio)pyrazine-2-carbonitrile;

3-(5-(Isobutylthio)-1,3,4-thiadiazol-2-ylthio)pyrazine-2-carbonitrile;

3-(5-(Pentylthio)-1,3,4-thiadiazol-2-ylthio)pyrazine-2-carbonitrile;

3-(5-(Dodecylthio)-1,3,4-thiadiazol-2-ylthio)pyrazine-2-carbonitrile;

3-(5-(Benzylthio)-1,3,4-thiadiazol-2-ylthio)pyrazine-2-carbonitrile;

3-(5-Mercapto-1,3,4-thiadiazol-2-ylthio)pyrazine-2-carbonitrile;

3-(5-(Isopropylthio)-4-methyl-4H-1,2,4-triazol-3-ylthio) pyrazine-2-carbonitrile;

3-(5-(Methylthio)-1,2,4-thiadiazol-3-ylthio)pyrazine-2-carbonitrile;

3-(5-Methyl-1,3,4-thiadiazol-2-ylthio)pyrazine-2-carbonitrile;

3-(5-Butyl-1,3,4-thiadiazol-2-ylthio)pyrazine-2-carbonitrile;

3-(4-Methyl-4H-1,2,4-triazol-3-ylthio)pyrazine-2-carbonitrile;

3-(1-Methyl-1H-imidazol-2-ylthio)pyrazine-2-carbonitrile;

2-Chloro-3-(5-(methylthio)-1,3,4-thiadiazol-2-ylthio)pyrazine or a pharmaceutically acceptable salt thereof.

In one aspect, the invention provides the modified LCAT polypeptide, wherein the amino acid residue 31 is replaced by a cysteine residue, wherein the cysteine residue is modified by replacing the thiol hydrogen with 3-pyrazinyl-2-carbonitrile.

In another aspect, the invention contemplates the use of a pharmaceutical composition comprising the modified LCAT polypeptide, wherein the amino acid residue 31 is replaced by a cysteine residue, wherein the cysteine residue is modified by replacing the thiol hydrogen with 3-pyrazinyl-2-carbonitrile, and a pharmaceutically acceptable carrier.

Preparation of Compounds

The compounds of the present invention can be prepared using standard synthetic methods. For exemplary purposes, Scheme 1 illustrates methods for the preparation of compounds of structural formula (III). One of skill in the art will understand that similar methods can be used for the synthesis of compounds in the other structural classes.

As shown in Scheme 1, compounds of the present invention can be prepared beginning with the commercially available 2-chloropyrazinecarbonitrile (I). Treatment of I with a thiol, such as II in the presence of base such as NaH, $K_2CO_3$ or $CsCO_3$ in a suitable solvent such as THF, DMF or DMSO provides the adduct (III). Oxidation of the thio group in III with for example $H_2O_2$, oxone, or $MnO_2$ will give the sulfone or sulfoxide derivative. Alternatively, other oxidizing agents may be employed as described in March, J; Advanced Organic Chemistry, 5th ed., John Wiley & Sons, New York, pp. 1541 (2001).

Scheme 1

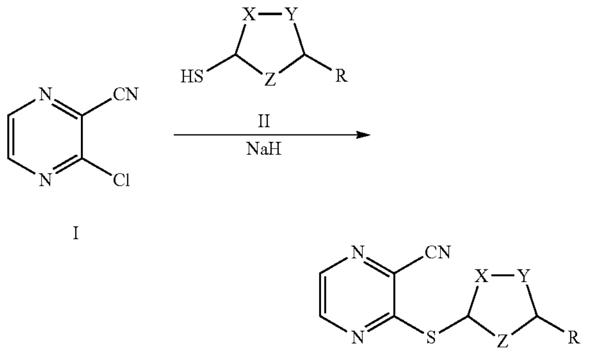

I

III

Other compounds of the present invention can be prepared beginning with 2,3-dichloropyrazine IV as shown in Scheme 2. Treatment of IV with a thiol, such as II in the presence of base such as NaH, $K_2CO_3$ or $CsCO_3$ in a suitable solvent such as THF, DMF or DMSO provides the adduct V. Compound V can also be converted to compounds of formula III by treatment with, for example, potassium cyanide or zinc cyanide in the presence of a palladium catalyst in a suitable solvent such as THF or DMF (see e.g. Y. Akita et al, Synthesis, 974, (1981)).

Scheme 2

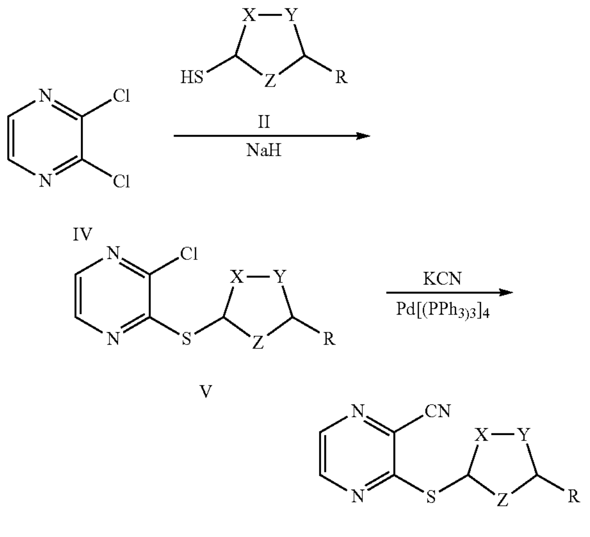

IV

V

III

Preparation of the Compounds of the Invention is Described in More Detail in Examples below.

III. Pharmaceutical Compositions Comprising Modified LCAT and Methods of Administration While it may be possible to administer compounds of the invention alone, in the methods described, the compound administered is generally present as an active ingredient in a desired dosage unit formulation, such as pharmaceutically acceptable composition containing conventional pharmaceutically acceptable carriers. Thus, in another aspect of the invention, there is provided a pharmaceutical composition comprising a compound of this invention in combination with a pharmaceutically acceptable carrier. Acceptable pharmaceutical carriers generally include diluents, excipients, adjuvants and the like as described herein.

A pharmaceutical composition of the invention may comprise an effective amount of a compound of the invention or an effective dosage amount of a compound of the invention. An effective dosage amount of a compound of the invention includes an amount less than, equal to, or greater than an effective amount of the compound. For example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound may be administered by administering a portion of the composition. "Unit dosage" is defined as a discrete amount of a therapeutic composition dispersed in a suitable carrier. Those of ordinary skill in the art will readily optimize effective dosages and administration regimens as determined by good medical practice and the clinical condition of the individual patient.

The pharmaceutical compositions may generally be prepared by mixing one or more compounds of Formula I including stereoisomers or tautomers, solvates, pharmaceutically acceptable salts, derivatives or prodrugs thereof, with pharmaceutically acceptable carriers, excipients, binders, adjuvants, diluents and the like, to form a desired administrable formulation to treat or ameliorate a variety of disorders related to atherosclerosis or cardiovascular diseases.

The pharmaceutical compositions may generally be prepared by mixing one or more LCAT compounds with one or more pharmaceutically acceptable carriers, excipients, binders, adjuvants, diluents, preservatives, solubilizers, emulsifiers and the like, to form a desired administrable formulation to treat or ameliorate a variety of diseases. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hyaluronic acid may also be used, and this may have the effect of promoting sustained duration in the circulation. Such compositions may influence the physical state, stability, rate of in vivo release, and rate of in vivo clearance of the present proteins and derivatives. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder, such as lyophilized form. Implantable sustained release formulations are also contemplated, as are transdermal formulations.

The pharmaceutical compositions may be subjected to conventional pharmaceutical operations such as sterilization and/or may contain conventional adjuvants, such as preservatives, stabilizers, wetting agents, emulsifiers, buffers etc. The pharmaceutically active compounds of this invention can be processed in accordance with conventional methods of pharmacy to produce medicinal agents for administration to patients, including humans and other mammals.

Pharmaceutical compositions can be manufactured by methods well known in the art such as conventional granulating, mixing, dissolving, encapsulating, lyophilizing, emulsifying or levigating processes, among others. The compositions can be in the form of, for example, granules, powders, tablets, capsules, syrup, suppositories, injections, emulsions, elixirs, suspensions or solutions. The instant compositions can be formulated for various routes of administration, for example, by oral administration, by transmucosal administration (including pulmonary and nasal administration), parenteral administration (including subcutaneous administration), transdermal (topical) administration or by rectal administration, as well as intrathecal, intravenous, intramuscular, intraperitoneal, intranasal, intraocular or intraventricular injection. The compound or compounds of the instant invention can also be administered in a local rather than a systemic fashion, such as injection as a sustained release formulation.

Besides those representative dosage forms described herein, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (2000); and "Pharmaceutics The Science of Dosage Form Design, $2^{nd}$ Ed. (Aulton, ed.) Churchill Livingstone (2002). The following dosage forms are given by way of example and should not be construed as limiting the invention.

A. Oral administration

For oral, buccal, and sublingual administration, powders, suspensions, granules, tablets, pills, capsules, gelcaps, troches or lozenges, cachets, pellets and caplets are acceptable as solid dosage (and unit dosage) forms and are described generally in Chapter 89 of Remington's Pharmaceutical Sciences (1990), 18th Ed., Mack Publishing Co. Easton Pa. 18042, which is herein incorporated by reference. Solid dosage forms also include liposomal or proteinoid encapsulation (for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given in Chapter 10 of Marshall, K., Modern Pharmaceutics (1979), edited by G. S. Banker and C. T. Rhodes, herein incorporated by reference. In general, the formulation includes the LCAT compound, and inert ingredients which allow for protection against the stomach environment, and release of the biologically active material in the intestine.

If necessary, the compounds are chemically modified to enhance bioefficacy of oral delivery. Generally, the chemical modification contemplated is the attachment of at least one moiety to the compound molecule itself, where said moiety permits (a) inhibition of proteolysis; and (b) uptake into the blood stream from the stomach or intestine. Also desired is the increase in overall stability of the compound and increase in circulation time in the body. Moieties useful as covalently attached vehicles in this invention may also be used for this purpose. Examples of such moieties include: PEG, copolymers of ethylene glycol and propylene glycol, carboxymethyl cellulose, dextran, polyvinyl alcohol, polyvinyl pyrrolidone and polyproline as well as other moieties described herein. See also, for example, Abuchowski and Davis, Soluble Polymer-Enzyme Adducts, Enzymes as Drugs (1981), Hocenberg and Roberts, eds., Wiley-Interscience, New York, N.Y., pp 367-83; Newmark, et al. (1982), J. Appl. Biochem. 4:185-9. Other polymers that could be used are poly-1,3-dioxolane and poly-1,3,6-tioxocane. In one aspect, PEG moieties are provided for pharmaceutical usage, as indicated above.

For oral delivery dosage forms, it is also possible to use a salt of a modified aliphatic amino acid, such as sodium N-(8-

[2-hydroxybenzoyl]amino) caprylate (SNAC), as a carrier to enhance absorption of the therapeutic compounds of this invention. The clinical efficacy of a heparin formulation using SNAC has been demonstrated in a Phase II trial conducted by Emisphere Technologies. See U.S. Pat. No. 5,792,451, "Oral drug delivery composition and methods".

The compounds of this invention can be included in the formulation as fine multiparticulates in the form of granules or pellets of particle size about 1 mm. The formulation of the material for capsule administration could also be as a powder, lightly compressed plugs or even as tablets. The therapeutic could be prepared by compression.

Oral pharmaceutical compositions contemplated can be prepared, for example, by mixing one or more compounds of the instant invention, or stereoisomers, solvates, prodrugs, pharmaceutically acceptable salts or tautomers thereof, with at least one additive or excipient such as a starch or other additive and tableted, encapsulated or made into other desirable forms for conventional administration. Suitable additives or excipients are sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Additionally, dyestuffs or pigments may be added for identification. Tablets and pills may be further treated with suitable coating materials known in the art.

Liquid dosage forms for oral administration may be in the form of pharmaceutically acceptable emulsions, syrups, elixirs, suspensions, slurries and solutions, which may contain an inactive diluent, such as water. Pharmaceutical formulations may be prepared as liquid suspensions or solutions using a sterile liquid, such as, but not limited to, an oil, water, an alcohol, and combinations of these. Pharmaceutically suitable surfactants, suspending agents, emulsifying agents, and the like may be added for oral or parenteral administration. More specifically, various aspects of oral pharmaceutical compositions include one or more of the following additives.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the compound of the invention with an inert material. These diluents could include carbohydrates, especially mannitol, -lactose, anhydrous lactose, cellulose, sucrose, modified dextrans and starch. Certain inorganic salts may also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrants include but are not limited to starch including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An antifrictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the compound of this invention into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethonium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Additives may also be included in the formulation to enhance uptake of the compound. Additives potentially having this property are for instance the fatty acids oleic acid, linoleic acid and linolenic acid.

Controlled release formulation may be desirable. The compound of this invention could be incorporated into an inert matrix which permits release by either diffusion or leaching mechanisms e.g., gums. Slowly degenerating matrices may also be incorporated into the formulation, e.g., alginates, polysaccharides. Another form of a controlled release of the compounds of this invention is by a method based on the Oros therapeutic system (Alza Corp.), i.e., the drug is enclosed in a semipermeable membrane which allows water to enter and push drug out through a single small opening due to osmotic effects. Some enteric coatings also have a delayed release effect.

Other coatings may be used for the formulation. These include a variety of sugars which could be applied in a coating pan. The therapeutic agent could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group consists of the enteric materials that are commonly esters of phthalic acid.

A mix of materials might be used to provide the optimum film coating. Film coating may be carried out in a pan coater or in a fluidized bed or by compression coating.

B. Pulmonary delivery forms

Also contemplated herein is pulmonary delivery of the present protein (or derivatives thereof). The protein (or derivative) is delivered to the lungs of a mammal while inhaling and traverses across the lung epithelial lining to the blood stream. (Other reports of this include Adjei et al., Pharma. Res. (1990) 7: 565-9; Adjei et al. (1990), Internatl. J. Pharmaceutics 63: 135-44 (leuprolide acetate); Braquet et al. (1989), J. Cardiovasc. Pharmacol. 13 (supp1.5): s.143-146 (endothelin-1); Hubbard et al. (1989), Annals Int. Med. 3: 206-12 (α1-antitrypsin); Smith et al. (1989), J. Clin. Invest. 84: 1145-6 (α1-proteinase); Oswein et al. (March 1990), "Aerosolization of Proteins", Proc. Symp. Resp. Drug Delivery II, Keystone, Colo. (recombinant human growth hormone); Debs et al. (1988), J. Immunol. 140: 3482-8 (interferon-γ and tumor necrosis factor α) and Platz et al., U.S. Pat. No. 5,284,656 (granulocyte colony stimulating factor).

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of the inventive compound. Typically, each formulation is specific to the type of device employed and may involve the use of an appropriate propellant material, in addition to diluents, adjuvants and/or carriers useful in therapy.

The inventive compound should most advantageously be prepared in particulate form with an average particle size of less than 10 μm (or microns), most preferably 0.5 to 5 μm, for most effective delivery to the distal lung.

Pharmaceutically acceptable carriers for pulmonary delivery include carbohydrates such as trehalose, mannitol, xylitol, sucrose, lactose, and sorbitol. Other ingredients for use in formulations may include DPPC, DOPE, DSPC and DOPC. Natural or synthetic surfactants may be used. PEG may be used (even apart from its use in derivatizing the protein or analog). Dextrans, such as cyclodextran, may be used. Bile salts and other related enhancers may be used. Cellulose and cellulose derivatives may be used Amino acids may be used, such as use in a buffer formulation.

Also, the use of liposomes, microcapsules or microspheres, inclusion complexes, or other types of carriers is contemplated.

Formulations suitable for use with a nebulizer, either jet or ultrasonic, will typically comprise the inventive compound dissolved in water at a concentration of about 0.1 to 25 mg of biologically active protein per mL of solution. The formulation may also include a buffer and a simple sugar (e.g., for protein stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device will generally comprise a finely divided powder containing the inventive compound suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing the inventive compound and may also include a bulking agent, such as lactose, sorbitol, sucrose, mannitol, trehalose, or xylitol in amounts which facilitate dispersal of the powder from the device, e.g., 50 to 90% by weight of the formulation.

C. Nasal administration

Nasal delivery of the inventive compound is also contemplated. Nasal delivery allows the passage of the protein to the blood stream directly after administering the therapeutic product to the nose, without the necessity for deposition of the product in the lung. Formulations for nasal delivery include those with dextran or cyclodextran. Delivery via transport across other mucous membranes is also contemplated.

For nasal administration, the pharmaceutical formulations may be a spray or aerosol containing an appropriate solvent and optionally other compounds such as, but not limited to, stabilizers, antimicrobial agents, antioxidants, pH modifiers, surfactants, bioavailability modifiers and combinations of these. A propellant for an aerosol formulation may include compressed air, nitrogen, carbon dioxide, or a hydrocarbon based low boiling solvent. The compound or compounds of the instant invention are conveniently delivered in the form of an aerosol spray presentation from a nebulizer or the like.

D. Parenteral administration

Injectable dosage forms for parenteral administration generally include aqueous suspensions or oil suspensions, which may be prepared using a suitable dispersant or wetting agent and a suspending agent. Injectable forms may be in solution phase or a powder suitable for reconstitution as a solution. Both are prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides. For injection, the formulations may optionally contain stabilizers, pH modifiers, surfactants, bioavailability modifiers and combinations of these. The compounds may be formulated for parenteral administration by injection such as by bolus injection or continuous infusion. A unit dosage form for injection may be in ampoules or in multi-dose containers.

E. Rectal Administration

For rectal administration, the pharmaceutical formulations may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is solid phase at room temperature but liquid phase at those temperatures suitable to release a drug inside the body, such as in the rectum. Various other agents and additives may be used in the preparation of suppositories as is well known to those of skill in the art.

F. Forms

The formulations of the invention may be designed to be short-acting, fast-releasing, long-acting, and sustained-releasing as described below. Thus, the pharmaceutical formulations may also be formulated for controlled release or for slow release. The instant compositions may also comprise, for example, micelles or liposomes, or some other encapsulated form, or may be administered in an extended release form to provide a prolonged storage and/or delivery effect. Therefore, the pharmaceutical formulations may be compressed into pellets or cylinders and implanted intramuscularly or subcutaneously as depot injections or as implants such as stents. Such implants may employ known inert materials such as silicones and biodegradable polymers.

G. Dosages

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

A therapeutically effective dose may vary depending upon the route of administration and dosage form. Typically, the compound or compounds of the instant invention are selected to provide a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

The dosage regimen for treating LCAT-mediated diseases and other diseases listed above with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, for example from about 0.1 mg to 10 mg/kg, or from about 0.25 mg to 1 mg/kg are useful for all methods of use disclosed herein. Generally, the daily regimen should be in the range of 0.1-1000 micrograms of the compound per kilogram of body weight, preferably 0.1-150 micrograms per kilogram.

For oral administration, the pharmaceutical composition may be in the form of, for example, a capsule, a tablet, a suspension, or liquid. The pharmaceutical composition can be made in the form of a dosage unit containing a given amount of the active ingredient. For example, these may contain an amount of active ingredient from about 1 to 2000 mg, for example from about 1 to 500 mg, or from about 5 to 150 mg, or from 10 to 100 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, such as from about 0.1 to about 10 mg/kg, or from about 0.25 mg to 1 mg/kg.

Formulations suitable for topical administration include liquid or semi-liquid preparations suitable for penetration through the skin (e.g., liniments, lotions, ointments, creams, or pastes) and drops suitable for administration to the eye, ear, or nose.

A suitable topical dose of active ingredient of a compound of the invention is 0.1 mg to 150 mg administered one to four, for example one or two times daily. For topical administration, the active ingredient may comprise from 0.001% to 10% w/w, e.g., from 1% to 2% by weight of the formulation, although it may comprise as much as 10% w/w, but typically not more than 5% w/w. In one aspect, the concentration is from 0.1% to 1% of the formulation.

H. Administration Regimens

Administration of the compositions can be systemic or local, and may comprise a single site injection of a therapeutically-effective amount of the modified LCAT polypeptide composition. Any route known to those of skill in the art for the administration of a therapeutic composition of the invention is contemplated including, for example, intravenous, intramuscular, subcutaneous or a catheter for long-term administration. Alternatively, it is contemplated that the therapeutic composition may be delivered to the patient at multiple sites. The multiple administrations may be rendered simultaneously or may be administered over a period of several hours. In certain cases, it may be beneficial to provide a continuous flow of the therapeutic composition. Additional therapy may be administered on a period basis, for example, daily, weekly, or monthly. In certain embodiments, the modified LCAT polypeptide is provided locally to the site of reperfusion.

IV. Methods of Treatment

A. Atherosclerosis, Cardiovascular Disease or an Associated Disease

In one aspect, the method of treatment of the invention is therapeutic, and compounds and compositions of the invention are administered to a subject already suffering from atherosclerosis, cardiovascular disease or an associated disease. In another aspect, methods of treatment are prophylactic and compounds and compositions are administered to those subjects at risk for developing atherosclerosis. To determine whether a subject is at risk of, for example atherosclerosis, an atherogenic lipoprotein profile can be assessed. For example, a ratio of serum cholesterol to HDLs of 5:1 or above indicates a higher than average risk of developing atherosclerosis. Other factors include a serum cholesterol level of 240 mg/dL or above, an HDL level 35 mg/dL or below, or an LDL level 190 mg/dL or above, a plasma LCAT protein level lower than normal (<5 ug/ml), and a decreased plasma cholesterol esterification rate (<60 nmol/ml/hr).

The amount of the modified LCAT effective to decrease accumulation of cholesterol depends on several factors, including the species, the manner of administration, the general health of the subject, the desired result (e.g., prophylaxis or therapeutic treatment) and the judgment of the prescribing physician. For example, the practitioner may decide what risk levels for heart disease indicate prophylactic treatment, and what target level of the modified LCAT is indicated for the treatment of a person already suffering from atherosclerosis.

In humans, the normal cholesterol esterification rate ranges from about 60 nmol/ml/hr to about 130 nmol/mL per hour. The effective treatment of atherosclerosis in humans can involve administration of the compositions of the invention to achieve a cholesterol esterification rate of about 200 nmol/ml/hr.

The invention provides methods for the treatment, prevention, or management of a cardiovascular disease. As used herein, the term "cardiovascular diseases" refers to diseases of the heart and circulatory system. Cardiovascular diseases which the compositions of the present invention are useful for preventing or treating include but are not limited to arteriosclerosis; atherosclerosis; stroke; ischemia; endothelium dysfunctions, in particular those dysfunctions affecting blood vessel elasticity; peripheral vascular disease; coronary heart disease; myocardial infarction, cerebral infarction and restenosis, thrombosis, high blood pressure and angina. Other diseases which the compositions of the present invention are useful for preventing or treating include LCAT deficiency syndrome, Alzheimer's disease, corneal opacity, metabolic syndrome, dyslipidemia, myocardial infarction, stroke, critical limb ischemia.

B. Inflammatory Conditions

Methods, compounds and compositions of the invention are useful in suppressing inflammatory cell activation. The term "inflammatory cell activation," as used herein, means the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatibility antigens or cell adhesion molecules) in inflammatory cells (including but not limited to monocytes, macrophages, T lymphocytes, B Lymphocytes, granulocytes, polymorphonuclear leukocytes, mast cells, basophils, eosinophils, dendritic cells, and endothelial cells). It will be appreciated by persons skilled in the art that the activation of one or a combination of these phenotypes in these cells can contribute to the initiation, perpetuation, or exacerbation of an inflammatory condition.

Methods, compounds and compositions of the invention are useful in treating such diseases as arthritic diseases (such as rheumatoid arthritis), osteoarthritis, gouty arthritis, spondylitis, thyroid-associated ophthalmopathy, Behcet disease, sepsis, septic shock, endotoxic shock, gram negative sepsis, gram positive sepsis, toxic shock syndrome, asthma, chronic bronchitis, allergic rhinitis, allergic conjunctivitis, vernal conjunctivitis, eosinophilic granuloma, adult (acute) respiratory distress syndrome (ARDS), chronic pulmonary inflammatory disease (such as chronic obstructive pulmonary disease), silicosis, pulmonary sarcoidosis, reperfusion injury of the myocardium, brain or extremities, brain or spinal cord injury due to minor trauma, fibrosis including cystic fibrosis, keloid formation, scar tissue formation, atherosclerosis, autoimmune diseases, such as systemic lupus erythematosus (SLE) and transplant rejection disorders (e.g., graft vs. host (GvH) reaction and allograft rejection), chronic glomerulonephritis, inflammatory bowel diseases, such as Crohn's disease and ulcerative colitis, proliferative lymphocytic diseases, such as leukemias (e.g. chronic lymphocytic leukemia; CLL) (see Munoz et al., J. Exp. Med. 172:95-103 (1990); Mentz et al., Blood 88:2172-2182 (1996)), and inflammatory dermatoses, such as atopic dermatitis, psoriasis, or urticaria.

C. Thrombosis-Related Conditions

It is also contemplated that the compounds, compositions and methods of the present invention are used in the treatment of a variety of disorders in which there is a need to prevent or treat thrombosis and subsequent decrease or loss of blood flow. The examples of thrombotic disorders include but not limited to atherosclerosis, myocardial infarction, stroke, and kidney ischemia, and thrombosis in any part of the mammalian body. The composition of the present invention will also be used in the prevention and treatment of microangiopathy in which formation of microthrombi or von Willebrand factor (VWF) binding to platelets causes excessive consumption of platelets and/or VWF leading to subsequent bleeding diathesis. Examples of latter disorders include but not limited to thrombotic thrombocytopenic purpura, type II and platelet type von Willebrand disease (VWD). The compounds or combination therapeutic methods of the present invention inhibit VWF-dependent platelet adhesion and aggregation. The compounds, compositions and methods are also useful in prolonging bleed time in a mammal and as such, are useful as anti-thrombotic agents both in therapeutic and prophylactic methods. As such, these compounds, compositions and methods are useful as anticoagulant agents and/or anti-platelet agents. Further, the present invention provides compounds, compositions and methods for the treatment of thrombosis and other disorders of the cardiovascular circulatory system that require and increase in the flow or reducing blockage of the vessels.

Compounds, compositions and methods are also useful for the treatment of any disorder that is presently treated using anticoagulant therapy. Such disorders include pulmonary embolism, unstable angina, myocardial infarction, deep vein thrombosis, atrial fibrillation with embolization, acute and chronic coagulopathies (disseminated intravascular coagulation), for prevention of clotting in arterial and cardiac surgery, for prophylaxis and treatment of peripheral arterial embolism, The compounds, compositions and methods are also used to treat thrombotic thrombocytopic purpura, other types of microangiopathy that are mediated by spontaneous interaction between VWF and platelets, platelet type or type IIb von Willebrand diseases in which there is an increased binding of VWF to platelets (either caused by a defect in GPIb or in VWF). The compounds, compositions and methods described herein are useful as anti-platelet agents in blood transfusions, extracorporeal circulation, dialysis procedures as well as blood sampling for laboratory procedures. The compounds, compositions and methods are also used to maintain the patency of an indwelling venipucture device that is being used for intermittent injection or infusion therapy or blood sampling. The compounds, compositions and methods are particularly useful in surgical procedures to prevent the formation of blood clots. Such indications are particularly desirable for patients undergoing abdominal surgery to reduce the risk of thromboembolic complications, patients undergoing knee or hip replacement therapy during and following the replacement procedure, as well as a general prophylactic to prevent clot formation at a later stage. The compounds, compositions and methods are further useful in the treatment of subjects that are under risk of thromboembolic complications due to severely restricted mobility e.g., during acute illness. Any such disorders may be readily treated by the compositions described herein. The therapeutic methods include both medical therapeutic and/or prophylactic administration, as appropriate.

As used herein, the term "inhibits platelet aggregation" includes its generally accepted meaning which includes prohibiting, slowing, or reducing the severity or degree of platelet aggregation. Such an inhibition may be measured as a function of time taken for a given sample to coagulate. In other embodiments, animal models of thrombosis. Methods of determining the efficacy of the agents include coagulation testing, monitoring the time of bleeding, determining hemoglobin levels of an animal and the like.

V. Combination Therapy

The invention further provides combination therapy, wherein the compounds and/or compositions of the invention are administered with one or more additional agent(s) In general, the therapeutic methods, compositions and compounds may also be employed in combination with other therapeutics in the treatment of various disease states, with the additional agents being administered concurrently or sequentially with a composition of the invention.

A. Cytokines

Exemplary cytokines or hematopoietic factors for such co-administration include IL-1 alpha, IL-1 beta, IL-2, IL-3, IL-4, IL-5, IL-6, IL-11, colony stimulating factor-1 (CSF-1), M-CSF, SCF, GM-CSF, granulocyte colony stimulating factor (G-CSF), EPO, interferon-alpha (IFN-alpha), consensus interferon, IFN-beta, IFN-gamma, IFN-omega, IL-7, IL-8, IL-9, IL-10, IL-12, IL-13, IL-14, IL-15, IL-16, IL-17, IL-18, IL-19, IL-20, IL-21, IL-22, IL-23, IL-24, IL-31, IL-32 alpha, IL-33, thrombopoietin (TPO), angiopoietins, for example Ang-1, Ang-2, Ang-4, Ang-Y, the human angiopoietin-like polypeptides ANGPTL1 through 7, vitronectin, vascular endothelial growth factor (VEGF), angiogenin, activin A, activin B, activin C, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, bone morphogenic protein receptor II, brain derived neurotrophic factor, cardiotrophin-1, ciliary neutrophic factor, ciliary neutrophic factor receptor, cripto, cryptic, cytokine-induced neutrophil chemotactic factor 1, cytokine-induced neutrophil, chemotactic factor 2α, cytokine-induced neutrophil chemotactic factor 2β, β endothelial cell growth factor, endothelin 1, epidermal growth factor, epigen, epiregulin, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor 11, fibroblast growth factor 12, fibroblast growth factor 13, fibroblast growth factor 16, fibroblast growth factor 17, fibroblast growth factor 19, fibroblast growth factor 20, fibroblast growth factor 21, fibroblast growth factor acidic, fibroblast growth factor basic, glial cell line-derived neutrophic factor receptor al, glial cell line-derived neutrophic factor receptor α2, growth related protein, growth related protein α, growth related protein β, growth related protein γ, heparin binding epidermal growth factor, hepatocyte growth factor, hepatocyte growth factor receptor, hepatoma-derived growth factor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor nerve growth factor receptor, neuropoietin, neurotrophin-3, neurotrophin-4, oncostatin M (OSM), placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor α, platelet derived growth factor receptor β, pre-B cell growth stimulating factor, stem cell factor (SCF), stem cell factor receptor, TNF, including TNF0, TNF1, TNF2, transforming growth factor α, transforming growth factor β, transforming growth factor β1, transforming growth factor β1.2, transforming growth factor β2, transforming growth factor β3, transforming growth factor β5, latent transforming growth factor β1, transforming growth factor β binding protein I, transforming growth factor β binding protein II, transforming growth factor β binding protein III, thymic stromal lymphopoietin (TSLP), tumor necrosis factor receptor type I, tumor necrosis factor receptor type II, urokinase-type plasminogen activator receptor, vascular endothelial growth factor, and chimeric proteins and biologically or immunologically active fragments thereof.

B. Atherosclerosis Drugs

Additional active agents may act in complementary or synergistic ways with the modified LCAT when used to treat, and prevent atherosclerosis or manage cholesterol, or related disorders such as cardiovascular disease.

In one aspect, compounds of the invention can be used with statins. Statins are drugs that competitively inhibit 3-hydroxy-3-methylglutaryl coenzyme A reductase "HMG-CoA reductase," which is the enzyme that catalyzes an early, rate-limiting step in cholesterol biosynthesis. Hebert et al., JAMA 1997, 278: 313-21. This combination, in addition to raising HDL levels and lowering LDL levels may also lowers triglyceride and reduce inflammation. It is believed that the combination can have additional therapeutic effects, for example, the combination may lower blood pressure; protect against heart disease, for example, by reducing smooth muscle proliferation, reduce heart attacks, reduce platelet aggregation, and to reduce strokes as well as peripheral arterial disease (clogging of the arteries to the legs).

Examples of statins of the invention include, but are not limited to, mevastatin, pitavastatin, rosuvastatin, pentostatin (Nipent®), nystatin, lovastatin (Mevacor®), simvastatin (Zocor®), pravastatin (Pravachol®), fluvastatin (Lescol®), atorvastatin (Lipitor®), cerivastatin (Baycol®), or combinations thereof. Statins suitable for use in the compositions and methods of the invention are also disclosed in U.S. Pat. Nos. 4,681,893; 5,273,995; 5,356,896; 5,354,772; 5,686,104; 5,969,156; and 6,126,971. As some statins may exist in an inactive form, such as a lactone (e.g., simvastatin), the invention encompasses using the active form (e.g., b-hydroxy acid form) of them. See Physicians Desk Reference, 54.sup.th Ed. (2000) pp. 1917-1920.

Fibrates or fabric acid derivatives are regarded as broad-spectrum lipid-modulating agents in that although their main action is to decrease serum triglycerides they also tend to reduce LDL-cholesterol and to raise HDL-cholesterol. It is believed that the combined use of compounds of the invention and a fibrate may reduce the risk of coronary heart disease events in those with low HDL-cholesterol or with raised triglycerides by speeding up the chemical breakdown (i.e., catabolism) of triglyceride-rich lipoproteins that circulate in the body.

Fibrates include, but are not limited to, bezafibrate, ciprofibrate, fenofibrate, gemfibrozil, clofibrate, or combinations thereof. Fibrates suitable for inclusion in the compositions or administration in the methods of the invention are disclosed in U.S. Pat. Nos. 4,895,762; 6,074,670; and 6,277,405.

Biguanides for use in the compositions and methods of the invention include, but are not limited to, metformin, phenformin, buformin, or combinations thereof. Biguanides suitable for use in the compositions or methods of the invention are also disclosed in U.S. Pat. No. 6,303,146. The combined use of compounds of the invention and a biguanide may improve glycemic control by enhancing insulin sensitivity in the liver and in muscle. The combination may reduce or avoid cardiovascular risk factors such as dyslipidemia, elevated plasminogen activator inhibitor 1 levels, other fibrinolytic abnormalities, hyperinsulinemia, insulin resistance, and is an effective and safe therapeutic agent for the treatment of type 2 diabetes.

In another aspect, compounds of the invention may be used in combination with glitazones, which may increase glucose uptake in muscle and reduced endogenous glucose production. Glitazones include 5-((4-(2-(methyl-2-pyri-dinyl amino)ethoxy)-phenyl)methyl)-2,4-thiazolidinedione, troglitazone, pioglitazone, ciglitazone, WAY-120,744, englitazone, AD 5075, darglitazone, rosiglitazone, combinations thereof, or a pharmaceutically acceptable salt, solvate, clathrate, polymorph, prodrug, or pharmacologically active metabolite thereof. Glitazones suitable for use in the compositions or methods of the invention are disclosed in U.S. Pat. Nos. 4,687,777; 5,002,953; 5,741,803; 5,965,584; 6,150,383; 6,150,384; 6,166,042; 6,166,043; 6,172,090; 6,211,205; 6,271,243; 6,288,095; 6,303,640; and 6,329,404.

Compositions comprising compounds of the invention and a sulfonylurea or a derivative thereof may increase insulin release from the pancreas and may further insulin levels by reducing hepatic clearance of the hormone. Sulfonylurea-based drugs for use the compositions and methods of the invention include, but are not limited to, glisoxepid, glyburide, acetohexamide, chlorpropamide, glibomuride, tolbutamide, tolazamide, glipizide, gliclazide, gliquidone, glyhexamide, phenbutamide, tolcyclamide, combinations thereof, or a pharmaceutically acceptable salt, solvate, or clathrate.

Combination compositions may also include agents that inhibit CETP. Such agents are, for example, Torcetrapib, and S-(2[([1-(2-ethylbutyl)cyclohexyl]carbonyl)amino]phenyl) 2-methylpropanethioate.

Additional active agents also include cardiovascular drugs. Cardiovascular drugs for use in combination with the compounds of the invention to prevent or treat cardiovascular diseases include peripheral antiadrenergic drugs, centrally acting antihypertensive drugs (e.g., methyldopa, methyldopa HCl), antihypertensive direct vasodilators (e.g., diazoxide, hydralazine HCl), drugs affecting renin-angiotensin system, peripheral vasodilators, phentolamine, antianginal drugs, cardiac glycosides, inodilators (e.g., amrinone, milrinone, enoximone, fenoximone, imazodan, sulmazole), antidysrhythmic drugs, calcium entry blockers, ranitine, bosentan, and rezulin.

Depending on the disorder for which treatment is sought, compounds and compositions of the invention are used in combination therapy with other therapeutics that achieve a specific biological effect.

1. Cholesterol Lowering Drugs

Various medications can lower blood cholesterol levels. They may be prescribed individually or in combination with other drugs. Some of the common types of cholesterol-lowering drugs include statins, resins and nicotinic acid (niacin), gemfibrozil and clofibrate. Thus, combination therapy is contemplated utilizing, for example, clofibrate (Atromid-S, which raises the HDL cholesterol levels and lowers triglyceride levels), gemfibrozil (Lopid, which raises HDL cholesterol levels), nicotinic acid (which works in the liver by affecting the production of blood fats and is used to lower triglycerides and LDL cholesterol, and raise HDL ("good") cholesterol), resins (which are also called bile acid-binding drugs and work in the intestines by promoting increased disposal of cholesterol), including cholestyramine (Questran, Prevalite, Lo-Cholest), colestipol (Colestid) and colesevelam (WelChol), and statins including atorvastatin (Lipitor), fluvastatin (Lescol), lovastatin (Mevacor), pravastatin (Pravachol), rosuvastatin calcium (Crestor), and simvastatin (Zocor).

The drugs of first choice for elevated LDL cholesterol are the HMG CoA reductase inhibitors, e.g., atorvastatin, fluvastatin, lovastatin, pravastatin, rosuvastatin and simvastatin. Statin drugs are effective for lowering LDL cholesterol levels, have few immediate short-term side effects, are easy to administer, have high patient acceptance and have few drug-drug interactions.

Another class of drugs for lowering LDL is the bile acid sequestrants—colesevelam, cholestyramine and colestipol—and nicotinic acid (niacin), which have been shown to reduce the risk for coronary heart disease in controlled clinical trials. Both classes of drugs appear to be free of serious side effects. But both can have troublesome side effects and require considerable patient education to achieve adherence. Nicotinic acid is preferred in patients with triglyceride levels that exceed 250 mg/dL because bile acid sequestrants tend to raise triglyceride levels.

2. ACE Inhibitors

Angiotensin II causes blood vessels to contract and thereby narrows the blood vessels. The narrowing of the vessels increases the pressure within the vessels and can cause high blood pressure (hypertension). Angiotensin II is formed from angiotensin I in the blood by the enzyme, angiotensin converting enzyme (ACE). ACE inhibitors decrease the production of angiotensin II. As a result, the blood vessels enlarge or dilate, and the blood pressure is reduced. ACE inhibitors that available in the United States include captopril (Capoten), benazepril (Lotensin), enalapril (Vasotec), lisinopril (Prinivil, Zestril) fosinopril (Monopril), ramipril (Altace), perindopril (Aceon), quinapril (Accupril), moexipril (Univasc), and trandolapril (Mavik).

C. Anti-Inflammatory Drugs

In prevention and treatment of inflammation, combination therapy is contemplated with, for example, acetylsalicylic acid (Aspirin, Ecotrin), choline magnesium salicylate (Trilisate), diclofenac (Voltaren, Cataflam, Voltaren-XR), diflunisal (Dolobid), etodolac (Lodine), fenoprofen (Nalfon), flurbiprofen (Ansaid), ibuprofen (Advil, Motrin, Medipren, Nuprin), indomethacin (Indocin, Indocin-SR), ketoprofen (Orudis, Oruvail), meclofenamate (Meclomen), nabumetone (Relafen), naproxen (Naprosyn, Naprelan, Anaprox, Aleve), oxaprozin (Daypro), phenylbutazone (Butazolidine), piroxicam (Feldene), salsalate (Disalcid, Salflex), tolmetin (Tolectin), valdecoxib (Bextra), and COX-2 selective non-steroidal anti-inflammatory drugs (NSAIDs) including Bextra, Celebrex, Naproxen, and Vioxx. Prescription-only NSAIDs include ibuprofen (Brufen), aceclofenac (Preservex), acemetacin (Emflex), azapropazone (Rheumox), celecoxib (Celebrex), dexketoprofen (Keral), diclofenac (Voltarol, Diclomax, Arthrotec), diflusinal (Dolobid), etodolac (Lodine), fenbufen (Lederfen), fenoprofen (Fenopron), flurbiprofen (Froben), indometacin, ketoprofen (Orudis, Oruvail), mefenamic acid, meloxicam (Mobic), nabumetone (Relifex), naproxen (Naprosyn, Synflex), phenylbutazone (Butacote), piroxicam (Feldene), sulindac (Clinoril), tenoxicam (Mobiflex) and tiaprofenic acid (Surgam), D. Anti-Thrombosis Drugs In methods for prevention and treatment of thrombosis-related conditions, combination therapy is contemplated with anti-thrombosis drugs such as anticoagulant drugs, which inhibit the ability of blood to clot, or coagulate and include dalteparin (Fragmin), danaparoid (Orgaran), enoxaparin (Lovenox), heparin (various), tinzaparin (Innohep), warfarin (Coumadin), and lepirudin (Refludan), and antiplatelet drugs such as aspirin, ticlopidine (Ticlid), clopidogrel (Plavix), tirofiban (Aggrastat) and eptifibatide (Integrilin). Still other methods include the use of bivalirudin (selective and reversible thrombin inhibitor), argatroban (reversible inhibitor of thrombin), and low molecular weight heparins (LMWHs), including enoxaparin (Lovenox), dalteparin (Fragmin), ardeparin (Normiflo) fondaparinux and idraparinux. Still other anti-thrombosis drugs contemplated for use in methods of the invention include fragmin (dalteparin sodium injection) lovenox (enoxaparin sodium), Normiflo (ardeparin sodium), Orgaran (danaparoid sodium), indirect (Antithrombin-Dependent) FXa inhibitors such as fondaparinux (Arixtra®) and idraparinux, direct (Antithrombin-Independent) FXa inhibitors such as BAY 59-7939 [Bayer], DPC-423 [Bristol-Myers Squibb], DX-9065a [Daiichi], LY517717, razaxaban (DPC906), lepirudin (Refludan®), desirudin (Revasc®), bivalirudin (Hirulog®, Angiomax®), argatroban (Novastan®), melagatran, and ximelagatran (Exanta®).

It should be understood that the disorder that may be treated by the compositions of the present invention are limited only by the fact that the disorder needs a therapeutic intervention which inhibits platelet aggregation. The doses of the agent may be modified for each individual subject. For particular guidance on the routes of administration, and uses those of skill in the art are referred to the Physician's Desk Reference for generalized descriptions of formulations, routes of administration and patient monitoring used for agents such as Aggrastat™ (see e.g., entry at pages 1933-1937, PDR, 57th Edn., 2003), Aggrenox™ (see e.g., entry at pages 1023-1026, PDR, 57th Edn., 2003), Agrylin™ (see e.g., entry at pages 3142-3143, PDR, 57th Edn., 2003), Flolan™ (see e.g., entry at pages 1516-1521, PDR, 57th Edn., 2003), Integrilin™ (see e.g., entry at pages 2138-2142, PDR, 57th Edn., 2003), Presantine™ (see e.g., entry at pages 1052-2053, PDR, 57th Edn., 2003), Plavix™ (see e.g., entry at pages 1098-1101, PDR, 57th Edn., 2003), Pletal™ (see e.g., entry at pages 2780-2782, PDR, 57th Edn., 2003), REoPro™ (see e.g., entry at pages 1866-1870, PDR, 57th Edn., 2003), Coumadin™ (see e.g., entry at pages 1074-1079, PDR, 57th Edn., 2003), Fragmin™ (see e.g., entry at pages 2750-2754, PDR, 57th Edn., 2003), Hep-Lock™ (see e.g., entry at pages 1284-1288, PDR, 57th Edn., 2003), Lovenox™ (see e.g., entry at pages 739-744, PDR, 57th Edn., 2003), Miradon™ (see e.g., entry at pages 3051-3052, PDR, 57th Edn., 2003). These entries in the PDR are provided to show the level of skill in the art relating to formulating and using compositions as anticoagulants and anti-platelet agents.

It is understood that the application of the teachings of the present invention to a specific problem or situation will be within the capabilities of one having ordinary skill in the art in light of the teachings contained herein. Examples of the products of the present invention and representative processes for their isolation, use, and manufacture appear below.

The following examples are offered to more fully illustrate the invention, but are not to be construed as limiting the scope thereof.

Example 1

Synthesis of 3-(5-(methylthio)-1,3,4-thiadiazol-2-ylthio)pyrazine-2-carbonitrile

1

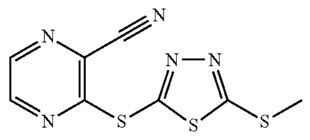

To a solution of 5-(methylthio)-1,3,4-thiadiazole-2-thiol (821 mg, 5.0 mmol) in DMF and benzene (10 ml, 1/1) was added NaH (60% dispersion in mineral oil, 220 mg, 5.5 mmol) slowly at 0° C. under nitrogen atmosphere. The resulting suspension was stirred at 0° C. for 15 minutes and then to the mixture was added 3-chloropyrazine-2-carbonitrile (698 mg, 5.0 mmol). The reaction was stirred at 80° C. for 4 hr. The reaction was then cooled to room temperature and quenched with saturated $NH_4Cl$ solution and extracted with EtOAc. The combined organic layers were washed with water, brine and dried over $MgSO_4$, filtered and the filtrate was concentrated. The residue was purified by chromatography on silica gel to give the title compound as a white solid.

$^1$H-NMR ($CDCl_3$) δ 2.83 (s, 3H), 8.54 (d, J=1.8 Hz, 1H), 8.58 (d, J=1.8 Hz, 1H). Mass Spectrum (ESI) m/e=268 ($M^+$+1).

Example 2

Synthesis of 3-(5-(ethylthio)-1,3,4-thiadiazol-2-ylthio)pyrazine-2-carbonitrile

2

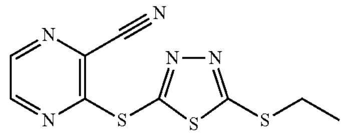

The title compound was prepared according to the procedure described in Example 1 by using 5-(ethylthio)-1,3,4-thiadiazole-2-thiol (592 mg, 3.33 mmol), NaH (60% dispersion in mineral oil, 146 mg, 3.66 mmol), and 3-chloropyrazine-2-carbonitrile (422 mg, 3.02 mmol) in DMF and benzene (8 ml, 1/1) by stirring at 90° C. under nitrogen atmosphere overnight.

$^1$H-NMR ($CDCl_3$) δ 1.56 (t, J=5.6 Hz, 3H), 3.41 (q, J=5.6 Hz, 2H), 8.47 (d, J=1.8 Hz, 1H), 8.52 (d, J=1.8 Hz, 1H). Mass Spectrum (ESI) m/e=(ESI) m/e=282 ($M^+$+1).

Example 3

Synthesis of 3-(5-(allylthio)-1,3,4-thiadiazol-2-ylthio)pyrazine-2-carbonitrile

3

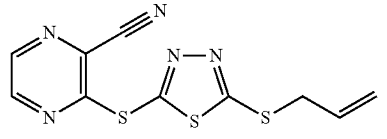

The title compound was prepared according to the procedure described in Example 1 by using 5-(allylthio)-1,3,4-thiadiazole-2-thiol (460 mg, 2.42 mmol), NaH (60% dispersion in mineral oil, 107 mg, 2.66 mmol), and 3-chloropyrazine-2-carbonitrile (338 mg, 2.42 mmol) in DMF and benzene (8 ml, 1/1) by stirring at 85° C. under nitrogen atmosphere overnight.

$^1$H-NMR ($CDCl_3$) δ 4.02 (d, J=10.4 Hz, 2H), 5.25 (d, J=10.4 Hz, 1H), 5.39 (d, J=15.6 Hz, 1H), 5.95-6.05 (m, 1H), 8.55 (d, J=1.8 Hz, 1H), 8.59 (d, J=1.8 Hz, 1H). Mass Spectrum (ESI) m/e=(ESI) m/e=294 ($M^+$+1).

Example 4

Synthesis of 3-(5-(propylthio)-1,3,4-thiadiazol-2-ylthio)pyrazine-2-carbonitrile

4

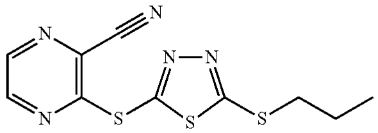

To a solution of 1,3,4-thiadiazole-2,5-dithiol (601 mg, 4.00 mmol) in DMF and benzene (6 ml, 1/1) was added NaH (60% dispersion in mineral oil, 176 mg, 4.40 mmol) slowly at 0° C. under nitrogen atmosphere. The resulting suspension was stirred at 0° C. for 15 minutes and then to the mixture was added bromopropane (492 mg, 2.00 mmol). The reaction was stirred at rt for 1 hr. To the reaction was added NaH (60% dispersion in mineral oil, 176 mg, 4.40 mmol) slowly at 0° C. and stirred for 15 minutes after addition. Then, 3-chloropyrazine-2-carbonitrile (557 mg, 4.00 mmol) was added to the mixture and the reaction was stirred at 50° C. under $N_2$ overnight. The reaction was then cooled to room temperature and quenched with saturated $NH_4Cl$ solution and extracted with EtOAc. The combined organic layers were washed with water, brine and dried over MgSO4. Removal of solvent gave the crude product which was purified by chromatography to give the title compound as an off-white solid.

$^1$H-NMR ($CDCl_3$) δ 1.08 (t, J=5.5 Hz, 3H), 1.8-1.9 (m, 2H), 3.37 (q, J=5.5 Hz, 2H), 8.52 (d, J=1.8 Hz, 1H), 8.58 (d, J=1.8 Hz, 1H). Mass Spectrum (ESI) m/e=296 ($M^+$+1).

Example 5

Synthesis of 3-(5-(butylthio)-1,3,4-thiadiazol-2-ylthio)pyrazine-2-carbonitrile

5

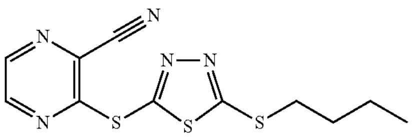

The title compound was prepared according to the procedure described in Example 4 by using 1,3,4-thiadiazole-2,5-dithiol (300 mg, 2.00 mmol), NaH (60% dispersion in mineral oil, 88 mg, 2.20 mmol), 1-iodobutane (0.263 ml, 2.30 mmol), NaH (60% dispersion in mineral oil, 88 mg, 2.20 mmol), and 3-chloropyrazine-2-carbonitrile (280 mg, 2.00 mmol) in DMF and benzene (8 ml, 1/1) by stirring at room temperature under nitrogen atmosphere overnight.

$^1$H-NMR ($CDCl_3$) δ 0.98 (t, J=7.6 Hz, 3H), 1.44-1.58 (m, 2H), 1.78-1.85 (m, 2H), 3.41 (t, J=7.6 Hz, 2H), 8.53 (d, J=2.4 Hz, 1H), 8.57 (d, J=2.4 Hz, 1H). Mass Spectrum (ESI) m/e=310 ($M^+$+1).

Example 6

Synthesis of 3-(5-(isobutylthio)-1,3,4-thiadiazol-2-ylthio)pyrazine-2-carbonitrile

6

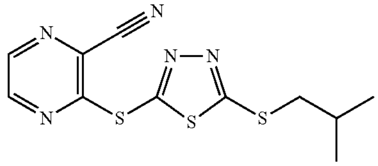

The title compound was prepared according to the procedure described in Example 4 by using 1,3,4-thiadiazole-2,5-dithiol (300 mg, 2.00 mmol), NaH (60% dispersion in mineral oil, 88 mg, 2.20 mmol), 1-bromo-2-methylpropane (0.25 ml, 2.30 mmol), NaH (60% dispersion in mineral oil, 88 mg, 2.20 mmol), and 3-chloropyrazine-2-carbonitrile (280 mg, 2.00 mmol) in DMF and benzene (8 ml, 1/1) by stirring at room temperature under nitrogen atmosphere overnight.

$^1$H-NMR ($CDCl_3$) δ 1.08 (dd, J=1.2, 6.8 Hz, 6H), 2.05-2.15 (m, 1H), 3.30 (t, J=5.6 Hz, 2H), 8.53 (d, J=2.4 Hz, 1H), 8.57 (d, J=2.4 Hz, 1H). Mass Spectrum (ESI) m/e=310 ($M^+$+1).

Example 7

Synthesis of 3-(5-(pentylthio)-1,3,4-thiadiazol-2-ylthio)pyrazine-2-carbonitrile

7

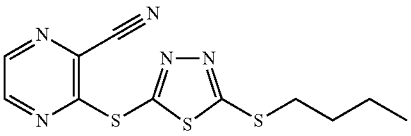

The title compound was prepared according to Example 4 by using 1,3,4-thiadiazole-2,5-dithiol (300 mg, 2.00 mmol), NaH (60% dispersion in mineral oil, 88 mg, 2.20 mmol), 1-iodopentane (0.30 ml, 2.30 mmol), NaH (60% dispersion in mineral oil, 88 mg, 2.20 mmol), and 3-chloropyrazine-2-carbonitrile (280 mg, 2.00 mmol) in DMF and benzene (8 ml, 1/1) by stirring at room temperature under nitrogen atmosphere overnight.

$^1$H-NMR ($CDCl_3$) δ 0.92 (t, J=7.6 Hz, 3H), 1.21-1.31 (m, 2H), 1.32-1.49 (m, 4H), 1.81-1.89 (m, 2H), 3.38 (t, J=6.8 Hz, 2H), 8.53 (d, J=2.4 Hz, 1H), 8.58 (d, J=2.4 Hz, 1H). Mass Spectrum (ESI) m/e=324 ($M^+$+1).

Example 8

Synthesis of 3-(5-(dodecylthio)-1,3,4-thiadiazol-2-ylthio)pyrazine-2-carbonitrile

8

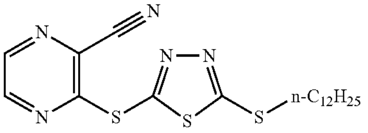

The title compound was prepared according to Example 1 by using 5-(dodecylthio)-1,3,4-thiadiazole-2-thiol (319 mg, 1.00 mmol), NaH (60% dispersion in mineral oil, 44 mg, 1.10 mmol), and 3-chloropyrazine-2-carbonitrile (140 mg, 1.00 mmol) in DMF and benzene (6 ml, 1/1) by stirring at room temperature under nitrogen atmosphere overnight.

$^1$H-NMR ($CDCl_3$) δ 0.89 (t, J=5.4, 3H), 1.2-1.4 (m, 18H), 1.4-1.5 (m, 2H), 1.8-1.9 (m, 2H), 3.39 (t, J=5.4, 2H), 8.54 (d, J=1.8 Hz, 1H), 8.58 (d, J=1.8 Hz, 1H). Mass Spectrum (ESI) m/e=422 ($M^+$+1).

Example 9

Synthesis of 3-(5-(benzylthio)-1,3,4-thiadiazol-2-ylthio)pyrazine-2-carbonitrile

9

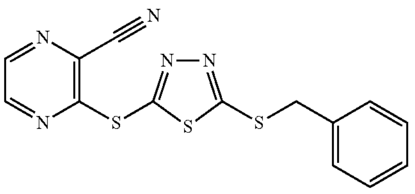

To a solution of 5-(benzylthio)-1,3,4-thiadiazole-2-thiol (240 mg, 1.00 mmol) in DMF and benzene (4 ml, 1/1) was added NaH (60% dispersion in mineral oil, 44 mg, 1.10 mmol) slowly at 0° C. under a nitrogen atmosphere. The resulting suspension was stirred at 0° C. for 15 minutes and then to the mixture was added 3-chloropyrazine-2-carbonitrile (140 mg, 1.00 mmol). The reaction was stirred at room temperature for 2 hr. The reaction was quenched with saturated $NH_4Cl$ solution and extracted with EtOAc. The combined organic layers were washed with water, brine and dried over $MgSO_4$. Removal of the solvent gave the crude product which was purified by chromatography to give the title compound as off-white solid.

$^1$H-NMR ($CDCl_3$) δ 4.63 (s, 2H), 7.20-7.43 (m, 5H), 8.54 (d, J=1.8 Hz, 1H), 8.56 (d, J=1.8 Hz, 1H). Mass Spectrum (ESI) m/e=344 ($M^+$+1).

Example 10

Synthesis of 3-(5-mercapto-1,3,4-thiadiazol-2-ylthio) pyrazine-2-carbonitrile

10

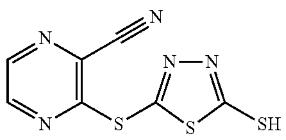

The title compound was prepared according to the procedure described in Example 1 by using 1,3,4-thiadiazole-2,5-dithiol (945 mg, 6.05 mmol), NaH (60% dispersion in mineral oil, 264 mg, 6.60 mmol), and 3-chloropyrazine-2-carbonitrile (840 mg, 6.00 mmol) in DMF and benzene (10 ml, 1/1) by stirring at 50° C. under nitrogen atmosphere for 4 hr.

$^1$H-NMR (DMSO) δ 8.77 (s, 1H), 8.88 (s, 1H). Mass Spectrum (ESI) m/e=254 ($M^+$+1).

Example 11

Synthesis of 3-(5-(isopropylthio)-4-methyl-4H-1,2,4-triazol-3-ylthio)pyrazine-2-carbonitrile

11

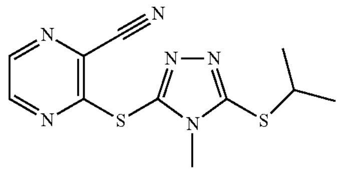

The title compound was prepared according to Example 1 by using 5-(isopropylthio)-4-methyl-4H-1,2,4-triazole-3-thiol (379 mg, 2.00 mmol), NaH (60% dispersion in mineral oil, 88 mg, 2.20 mmol), and 3-chloropyrazine-2-carbonitrile (280 mg, 2.00 mmol) in DMF and benzene (6 ml, 1/1) by stirring at room temperature under nitrogen atmosphere for 2 hr.

$^1$H-NMR ($CDCl_3$) δ 1.49 (d, J=5.4 Hz, 6H), 3.57 (s, 3H), 4.01 (m, 1H), 8.43 (d, J=1.8 Hz, 1H), 8.48 (d, J=1.8 Hz, 1H). Mass Spectrum (ESI) m/e=293 ($M^+$+1).

Example 12

Synthesis of 3-(5-(methylthio)-1,2,4-thiadiazol-3-ylthio)pyrazine-2-carbonitrile

12

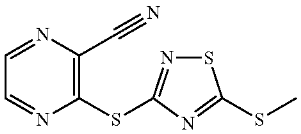

The title compound was prepared according to Example 1 by using 5-(methylthio)-1,2,4-thiadiazole-3-thiol (328 mg, 2.00 mmol), NaH (60% dispersion in mineral oil, 88 mg, 2.20 mmol), and 3-chloropyrazine-2-carbonitrile (280 mg, 2.00 mmol) in DMF and benzene (6 ml, 1/1) by stirring at room temperature under nitrogen atmosphere for 2 hr.

$^1$H-NMR ($CDCl_3$) δ 2.72 (s, 3H), 8.66 (d, J=1.8 Hz, 1H), 8.82 (d, J=1.8 Hz, 1H). Mass Spectrum (ESI) m/e=268 ($M^+$+1).

Example 13

Synthesis of 3-(5-methyl-1,3,4-thiadiazol-2-ylthio) pyrazine-2-carbonitrile

13

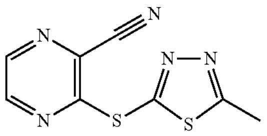

The title compound was prepared according to Example 1 by using 5-methyl-1,3,4-thiadiazole-2-thiol (264 mg, 2.00 mmol), NaH (60% dispersion in mineral oil, 88 mg, 2.20 mmol), and 3-chloropyrazine-2-carbonitrile (280 mg, 2.00 mmol) in DMF and benzene (6 ml, 1/1) by stirring at room temperature under nitrogen atmosphere for 6 hr.

$^1$H-NMR ($CDCl_3$) δ 2.86 (s, 3H), 8.52 (d, J=1.8 Hz, 1H), 8.55 (d, J=1.8 Hz, 1H). Mass Spectrum (ESI) m/e=236 ($M^+$+1).

Example 14

Synthesis of 3-(5-butyl-1,3,4-thiadiazol-2-ylthio) pyrazine-2-carbonitrile

14

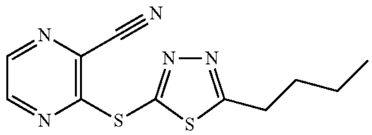

The title compound was prepared according to Example 1 by using 5-butyl-1,3,4-thiadiazole-2-thiol (260 mg, 1.49 mmol), NaH (60% dispersion in mineral oil, 66 mg, 1.65 mmol), and 3-chloropyrazine-2-carbonitrile (210 mg, 1.50 mmol) in DMF and benzene (4 ml, 1/1) by stirring at room temperature under nitrogen atmosphere for 3 hr.

$^1$H-NMR ($CDCl_3$) δ 1.01 (t, J=7.6 Hz, 3H), 1.42-1.49 (m, 2H), 1.81-1.91 (m, 2H), 3.19 (t, J=8.0 Hz, 2H), 8.53 (d, J=1.8 Hz, 1H), 8.57 (d, J=1.8 Hz, 1H). Mass Spectrum (ESI) m/e=278 ($M^+$+1).

Example 15

Synthesis of 3-(4-methyl-4H-1,2,4-triazol-3-ylthio) pyrazine-2-carbonitrile

15

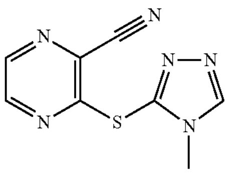

The title compound was prepared according to Example 1 by using 4-methyl-4H-1,2,4-triazole-3-thiol (230.5 mg, 2.00 mmol), NaH (60% dispersion in mineral oil, 88 mg, 2.20 mmol), and 3-chloropyrazine-2-carbonitrile (280 mg, 2.00 mmol) in DMF and benzene (6 ml, 1/1) by stirring at room temperature under nitrogen atmosphere for 4 hr.

$^1$H-NMR ($CDCl_3$) δ 3.75 (s, 3H), 8.43 (d, J=1.8 Hz, 1H), 8.48 (d, J=1.8 Hz, 1H). Mass Spectrum (ESI) m/e=219 ($M^+$+1).

Example 16

Synthesis of 3-(1-methyl-1H-imidazol-2-ylthio)pyrazine-2-carbonitrile

16

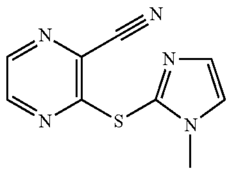

The title compound was prepared according to Example 1 by using 1-methyl-1H-imidazole-2-thiol (228 mg, 2.00 mmol), NaH (60% dispersion in mineral oil, 88 mg, 2.20 mmol), and 3-chloropyrazine-2-carbonitrile (280 mg, 2.00 mmol) in DMF and benzene (6 ml, 1/1) by stirring at room temperature under nitrogen atmosphere for 4 hr.

$^1$H-NMR ($CDCl_3$) δ 3.74 (s, 3H), 7.22 (d, J=1.6 Hz, 1H), 7.28 (d, J=1.6 Hz, 1H), 8.40 (d, J=1.8 Hz, 1H), 8.44 (d, J=1.8 Hz, 1H). Mass Spectrum (ESI) m/e=218 ($M^+$+1).

Example 17

Synthesis of 2-chloro-3-(5-(methylthio)-1,3,4-thiadiazol-2-ylthio)pyrazine

17

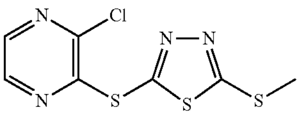

The title compound was prepared according the procedure described in Example 1 by using 5-(methylthio)-1,3,4-thiadiazole-2-thiol (1.64 g, 10.00 mmol), NaH (60% dispersion in mineral oil, 445 mg, 11.00 mmol), and 2,3-dichloropyrazine (1.04 ml, 10.00 mmol) in DMF and benzene (12 ml, 1/1) by stirring at 50° C. for 20 hr and then at 110° C. for 4 hr under nitrogen atmosphere.

$^1$H-NMR ($CDCl_3$) δ 2.85 (s, 3H), 8.22 (d, J=1.8 Hz, 1H), 8.35 (d, J=1.8 Hz, 1H). Mass Spectrum (ESI) m/e=277 ($M^+$+1).

Example 18

Isolation of LCAT

LCAT was isolated from culture media of CHO cells that were stably transfected with human LCAT cDNA. LCAT coding sequence was tagged with FLAG and HIS tages at the C-terminus Purification of tagged recombinant human LCAT protein was performed according to the standard protocol using Ni-NTA agarose beads. Briefly, CHO cultured media were incubated with Ni-NTA column at pH 8.0. The unbound proteins were washed from resin complex with 20 mM imidazole. The His-tagged protein was eluted with 250 mM imidazole and dialysed against 1×PBS containing 50 μM EDTA.

Example 19

LCAT Activity Assays

Activity of the modified LCAT of the invention and activities of compounds of the invention were determined by measuring change of the rate of conversion of $^3$H-labeled cholesterol to cholesteryl ester (CE). In the plasma LCAT activity assay, human plasma samples were equilibrated with a trace amount of radiolabeled cholesterol at 4° C. and the rate of cholesterol esterification was measured by TLC analysis after incubation at 37° C. (Dobiasova, supra). $EC_{50}$ represents a compound concentration achieving 50% of maximal activation of LCAT-mediated cholesterol esterification.

For measuring compound activity using apoAI-liposome assay format, full-length human LCAT cDNA was isolated from normal human liver cDNA library (BioChain, Hayward, Calif.) with standard protocol and cloned into a pCMV-Flag vector (See Example 18). Recombinant LCAT was expressed in CHO cells and the enzyme secreted from stably transfected cells was harvested in serum-free culture medium. Recombinant LCAT identity was confirmed with anti-human LCAT and anti-Flag antibodies. The activity of recombinant LCAT enzyme was determined using apoAI-liposome substrates prepared by the standard cholate-dialysis procedure (Chen et al. (1982) J. Lipid Res. 23: 680-691. The initial mixture contained egg PC/$^3$H-unesterfied cholesterol/human apoAI (molar ratio of 250:12.5:0.8). After dialysis the proteoliposomes were incorporated with recombinant LCAT protein. LCAT activity was determined by measuring the conversion of radiolabeled cholesterol to cholesteryl ester and expressed in nmol CE/mL per hour.

Example 20

LCAT Stability Measurements

LCAT enzyme stability was measured using the standard ELISA protocol. Briefly, LCAT protein molecules of the plasma samples were captured onto the ELISA plate with an anti-LCAT antibody which was pre-coated to the plate. After a careful wash to remove the unbound molecules, the LCAT protein was detected by using a second anti-LCAT antibody. The LCAT-antibody immunocomplexes were detected and quantified by using HRP detection system. Purified recombinant LCAT protein were used as standard and measured under the same experiment conditions (Kobori et al. (2002) J Lipid Res 43: 325-334).

Example 21

Assessment of the in vivo effects of the modified LCAT

Rodents used for assessing the in vivo effects of the compounds of the invention include BALB/c mice, CD1 mice, and Syrian hamsters of wild type fed with normal chew. These animals were treated with either vehicle or Compound A (3-(5-ethylthio)-1,3,4-thiadiazol-2-ylthio)pyrazine-2-carbonitrile) by IP injection. At time points (see Figures) after compound administration, blood samples were collected, plasma was immediately separated, and plasma levels of lipids, lipoprotein and LCAT activity were determined.

Results presented in FIG. 2(A) confirm activity and specificity of the compounds of the invention on LCAT enzyme. This experiment studied the effect of Compound A in LCAT-deficient plasma samples obtained from lcat mutant mice. Ng et al. (1997) J. Biol. Chem. 272:1 5777-81. No LCAT activity was detected in LCAT-deficient (lcat −/−) plasma samples in the presence or absence of Compound A, indicating that the observed interaction of Compound A with LCAT is highly specific.

Results summarized in FIG. 2(B) illustrate the mechanism of action of compounds of the invention on LCAT enzyme. Two loss-of-function LCAT mutants, H377A and S181A were generated, in which the critical catalytic triad of the enzyme was destroyed as described in Francone et al. (1991) Biochemistry 30: 10074-77; Peelman et al. (1998) Protein Sci. 7: 587-599; and Peelman et al. (2000) Curr. Opin. Lipidol. 11: 155-160. No activity was observed on either nonfunctional enzyme with or without Compound A (FIG. 2B). To test a hypothesis whether the mechanism of LCAT activation might involve the reaction of the molecule with a free thiol group in the enzyme, two other mutations in LCAT polypeptide targeting cysteine residues C31 and C184 were made. Neither of these two mutations significantly altered basal LCAT activity of the recombinant proteins. However, they exhibited distinct responses to Compound A. While the C184A mutant was able to respond to the treatment in a dose dependent manner comparable to that of the wild type enzyme, the C31A mutant failed to be activated by Compound A. This observation is consistent with the hypothesis that compounds of the invention bind irreversibly to LCAT at the amino acid residue 31 as measured in biochemical assays.

Figure 3:
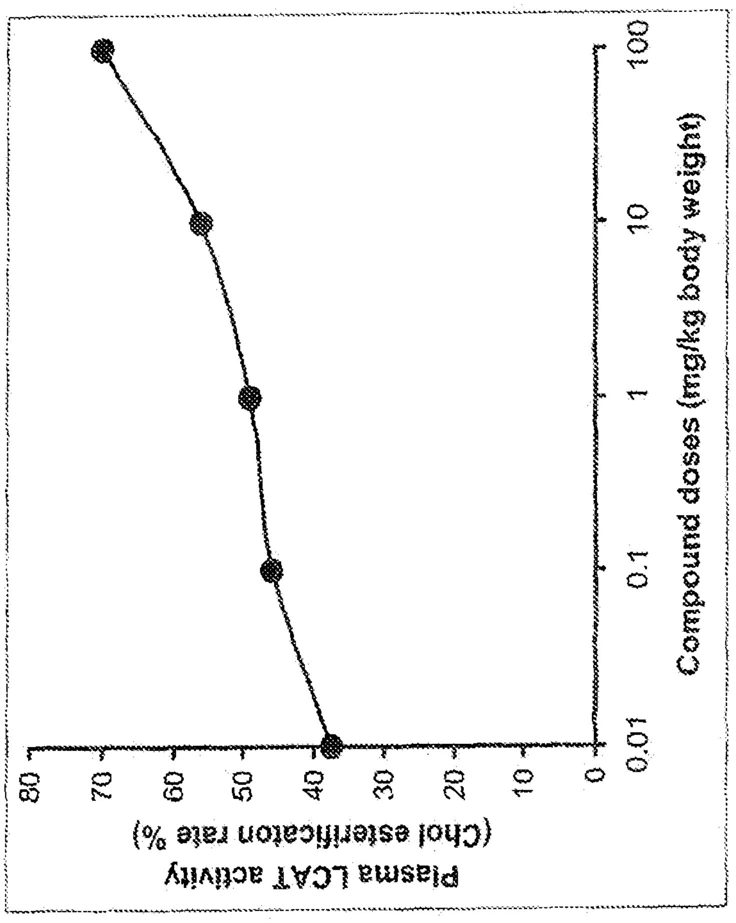
FIG. 3 summarizes data showing that compounds of the invention increase LCAT enzyme activity in a dose dependent manner in BALB/c mice.

FIG. 3 summarizes data showing that compounds of the invention increase LCAT enzyme activity in a dose dependent manner in BALB/c mice. Briefly, BALB/c mice (male, 7 weeks old) were treated with either vehicle or Compound A by intra-peritoneal (IP) in the indicated doses. Animals were fed normal chow diet. Compounds were solubilized in DEPG vehicle (containing 20% dimethyl acetamide, 10% ethanol, 50% polylene glycol) and administered to the animals. At the indicated time points, blood samples were taken from animals and plasma was separated immediately. An aliquot of plasma sample was labeled with $^3$H-cholesterol for the LCAT activity assay. Each data point represents the mean of samples from two individual animals. The remaining samples were used for plasma lipid and lipoprotein analyses.

Figure 4:
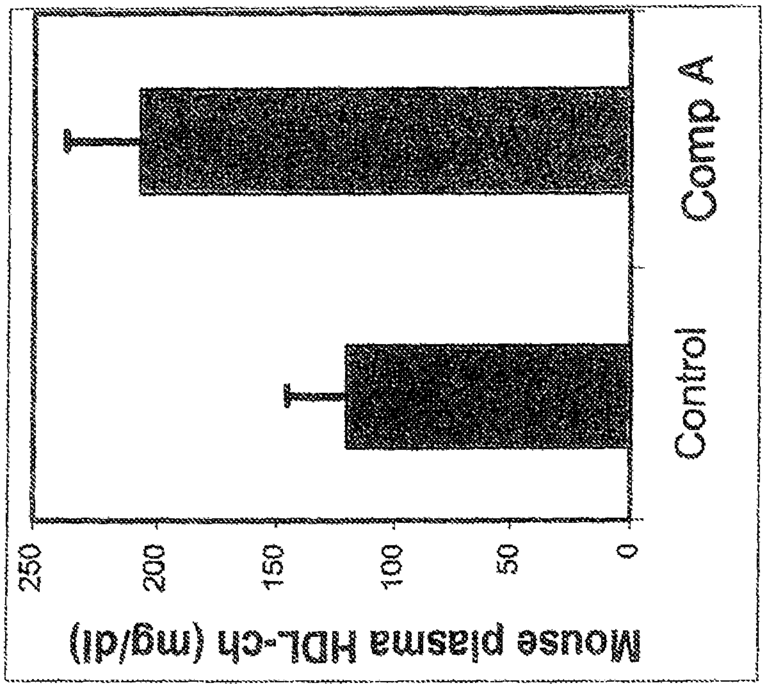
FIG. 4 demonstrates that treatment with the compounds of the invention increases HDL cholesterol levels in CD1 mice.

Results presented in FIG. 4 demonstrate that treatment with the compounds of the invention increases HDL cholesterol levels in CD1 mice. CD1 male three month old mice were treated with either vehicle (control) or with Compound A by IP injection (20 mg/kg, one dose per day, 4 days, n=8). Plasma samples were collected and HDL cholesterol concentrations were determined standard reagents and assay protocol using clinical analyzer (Infinity).

Figure 5:
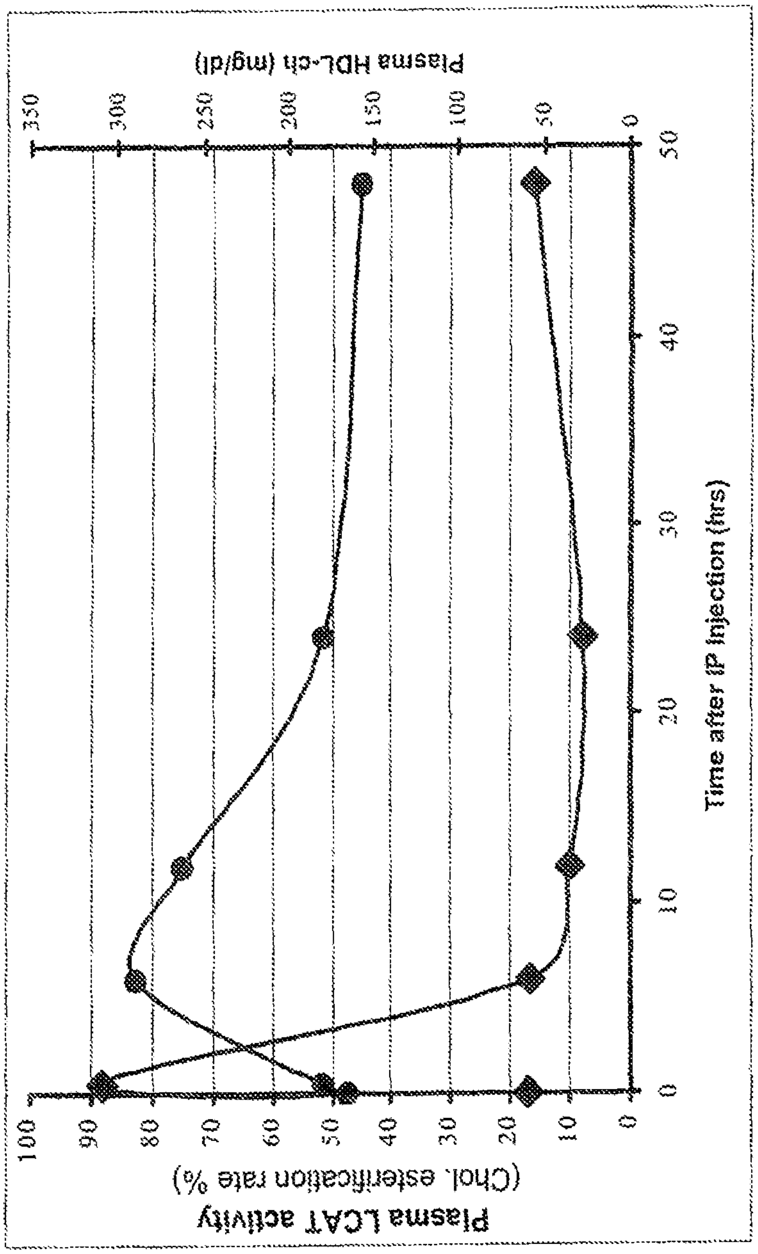
FIG. 5 illustrates the time course of LCAT activation and the levels of HDL in mice following a single doze of the compounds of the invention.

FIG. 5 illustrates the time course of LCAT activation and the levels of HDL in mice following a single doze of Compound A. Male three month old CD1 mice were given Compound A (20 mg/kg) by an IP injection. At each indicated time point, a group of animals (n=4) was sacrificed, blood samples were collected and plasma separated for measurement of LCAT activity (diamonds) and HDL (circles). Each data point represents the mean of measurement from four individual animals per treatment group.

Figure 6:
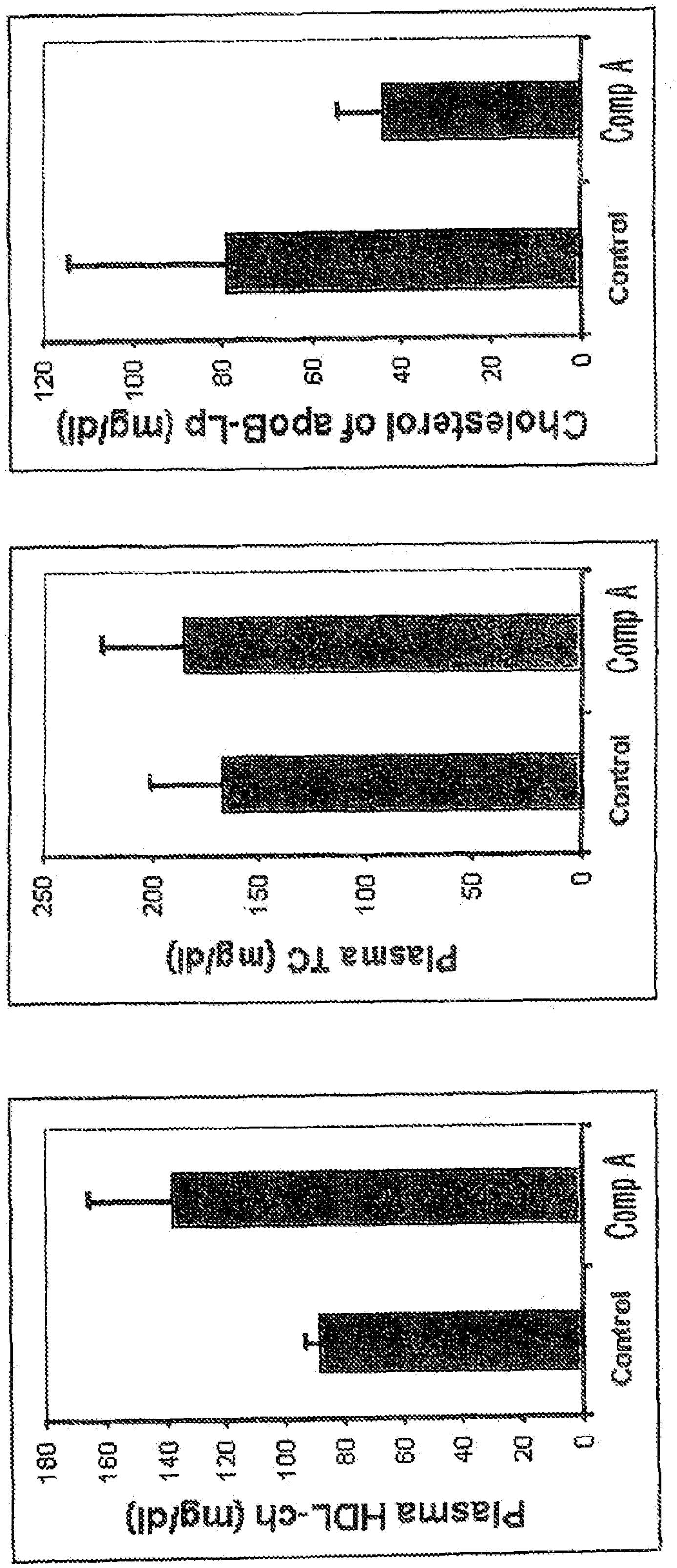
FIG. 6 demonstrates that treatment with the compounds of the invention increases HDL levels and decreases apoB-containing lipoprotein in vivo.

Results presented in FIG. 6 demonstrate that treatment with the compound of the invention increases HDL levels and decreases apoB-containing lipoprotein in vivo. Hamsters (Syrian, male, 12 weeks old, n=6 per group) were treated with either vehicle (control) or Compound A via IP administration (20 mg/kg, one dose per day, 4 days). Plasma samples were collected and concentrations of total cholesterol (TC), panel B, and HDL cholesterol (panel A) were measured. LpB cholesterol contents were obtained by subtracting HDL from TC (panel C).

Figure 7:
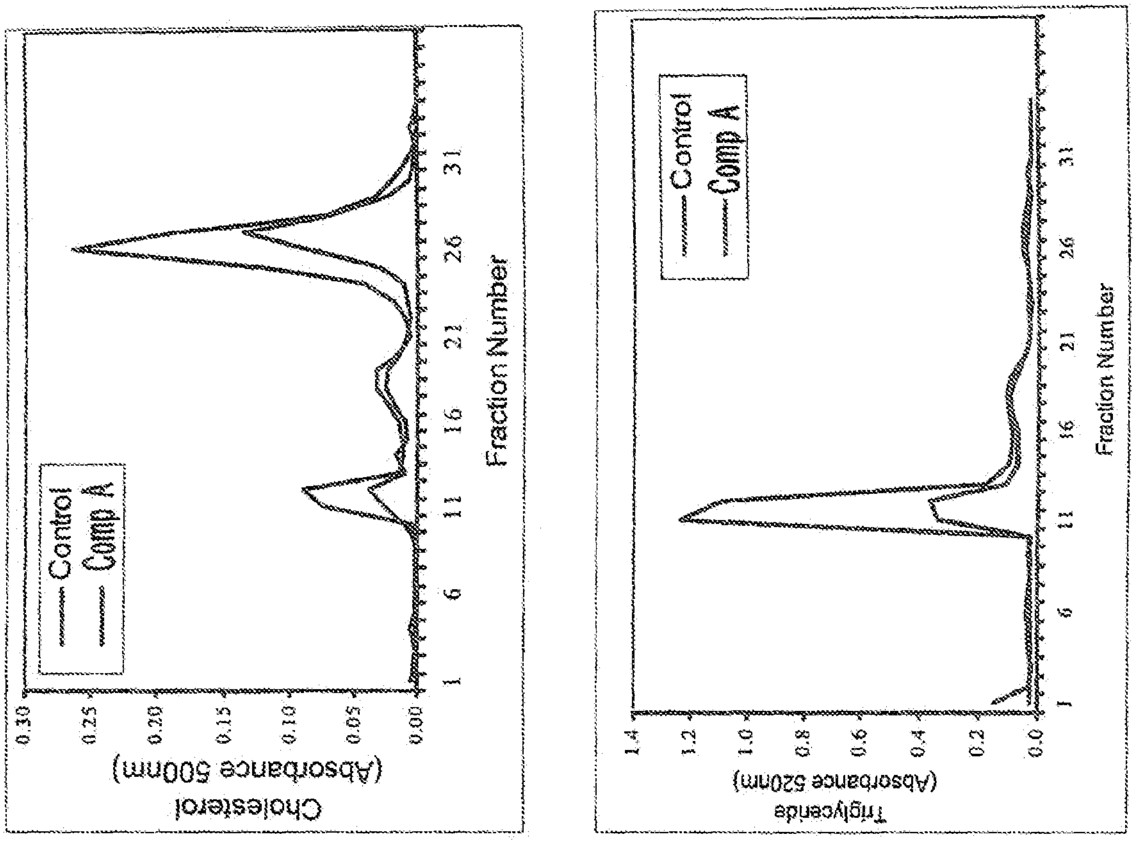
FIG. 7 provides elution profiles indicating that treatment with the compounds of the invention increases HDL-Ch levels, increases HDL particle size, and decrease TG levels in the VLDL fraction in vivo.

FIG. 7 provides elution profiles indicating that treatment with the compounds of the invention increases HDL-Ch levels, increases HDL particle size, and decrease TG levels in the VLDL fraction in vivo. Hamsters (n=6) were treated with either vehicle (control), or Compound A via IP administration (20 mg/kg/day, 4 days). Plasma samples were pooled within each treatment group, and separated by FPLC using two serially connected Superose 6 columns (Pharmacia Biotech Inc.). Cholesterol (panel A) and triglyceride (panel B) levels were determined in 0.5 ml fractions.

TABLE 1

HDL particle size profiles

| HDL subclass | Control | T865 |
|---|---|---|
| 2a | 12 | 39 |
| 2b | 58 | 56 |
| 3a | 28 | 3 |
| 3b | 1 | 1 |
| 3c | 1 | 1 |

Table 1 summarizes HDL particle size profiles as determined by Gradient Gel Electrophoresis (GGE) indicating an increase of HDL particle size in vivo after treating with the compounds of the invention. Hamsters were treated with either vehicle or Compound A as described above (20 mg/kg/day, 4 days, n=6). Plasma samples were collected and pooled for each group. An aliquot of pooled plasma was analyzed using GGE as described in Blanche et al. (1981) BBA 665: 408-419.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for treating atherosclerosis in a subject in need thereof, comprising administering a therapeutically effective amount of a modified mature human LCAT comprising a replacement of the amino acid residue 31 by a cysteine residue, wherein the cysteine residue is modified by replacing the thiol hydrogen with 3-pyrazinyl-2-carbonitrile.

2. The method of claim 1, wherein the modified mature human LCAT is administered intravenously.

3. The method of claim 2, wherein the modified mature human LCAT is administered by bolus.

4. A method for increasing HDL cholesterol in a subject comprising administering to the subject a pharmaceutical composition comprising a therapeutically effective amount of a modified mature human LCAT comprising a replacement of the amino acid residue 31 by a cysteine residue, wherein the cysteine residue is modified by replacing the thiol hydrogen with 3-pyrazinyl-2-carbonitrile, and a pharmaceutically acceptable carrier or excipient.

5. A pharmaceutical composition comprising a modified mature human LCAT comprising a replacement of the amino acid residue 31 by a cysteine residue, wherein the cysteine residue is modified by replacing the thiol hydrogen with 3-pyrazinyl-2-carbonitrile, and a pharmaceutically acceptable carrier.

6. The method of claim 1, wherein the subject is human.

* * * * *

SEQUENCE LISTING

```
<160> NUMBER OF SEQ ID NOS: 4

<210> SEQ ID NO 1
<211> LENGTH: 440
<212> TYPE: PRT
<213> ORGANISM: Homo sapiens

<400> SEQUENCE: 1

Met Gly Pro Pro Gly Ser Pro Trp Gln Trp Val Thr Leu Leu Leu Gly
1               5                   10                  15

Leu Leu Leu Pro Pro Ala Ala Pro Phe Trp Leu Leu Asn Val Leu Phe
            20                  25                  30

Pro Pro His Thr Thr Pro Lys Ala Glu Leu Ser Asn His Thr Arg Pro
        35                  40                  45

Val Ile Leu Val Pro Gly Cys Leu Gly Asn Gln Leu Glu Ala Lys Leu
    50                  55                  60

Asp Lys Pro Asp Val Val Asn Trp Met Cys Tyr Arg Lys Thr Glu Asp
65                  70                  75                  80

Phe Phe Thr Ile Trp Leu Asp Leu Asn Met Phe Leu Pro Leu Gly Val
                85                  90                  95

Asp Cys Trp Ile Asp Asn Thr Arg Val Val Tyr Asn Arg Ser Ser Gly
            100                 105                 110

Leu Val Ser Asn Ala Pro Gly Val Gln Ile Arg Val Pro Gly Phe Gly
        115                 120                 125

Lys Thr Tyr Ser Val Glu Tyr Leu Asp Ser Ser Lys Leu Ala Gly Tyr
    130                 135                 140

Leu His Thr Leu Val Gln Asn Leu Val Asn Asn Gly Tyr Val Arg Asp
145                 150                 155                 160

Glu Thr Val Arg Ala Ala Pro Tyr Asp Trp Arg Leu Glu Pro Gly Gln
                165                 170                 175

Gln Glu Glu Tyr Tyr Arg Lys Leu Ala Gly Leu Val Glu Glu Met His
            180                 185                 190

Ala Ala Tyr Gly Lys Pro Val Phe Leu Ile Gly His Ser Leu Gly Cys
        195                 200                 205

Leu His Leu Leu Tyr Phe Leu Leu Arg Gln Pro Gln Ala Trp Lys Asp
```

-continued

```
    210                 215                 220

Arg Phe Ile Asp Gly Phe Ile Ser Leu Gly Ala Pro Trp Gly Gly Ser
225                 230                 235                 240

Ile Lys Pro Met Leu Val Leu Ala Ser Gly Asp Asn Gln Gly Ile Pro
                245                 250                 255

Ile Met Ser Ser Ile Lys Leu Lys Glu Glu Gln Arg Ile Thr Thr Thr
            260                 265                 270

Ser Pro Trp Met Phe Pro Ser Arg Met Ala Trp Pro Glu Asp His Val
        275                 280                 285

Phe Ile Ser Thr Pro Ser Phe Asn Tyr Thr Gly Arg Asp Phe Gln Arg
    290                 295                 300

Phe Phe Ala Asp Leu His Phe Glu Glu Gly Trp Tyr Met Trp Leu Gln
305                 310                 315                 320

Ser Arg Asp Leu Leu Ala Gly Leu Pro Ala Pro Gly Val Glu Val Tyr
                325                 330                 335

Cys Leu Tyr Gly Val Gly Leu Pro Thr Pro Arg Thr Tyr Ile Tyr Asp
            340                 345                 350

His Gly Phe Pro Tyr Thr Asp Pro Val Gly Val Leu Tyr Glu Asp Gly
        355                 360                 365

Asp Asp Thr Val Ala Thr Arg Ser Thr Glu Leu Cys Gly Leu Trp Gln
    370                 375                 380

Gly Arg Gln Pro Gln Pro Val His Leu Leu Pro Leu His Gly Ile Gln
385                 390                 395                 400

His Leu Asn Met Val Phe Ser Asn Leu Thr Leu Glu His Ile Asn Ala
                405                 410                 415

Ile Leu Leu Gly Ala Tyr Arg Gln Gly Pro Pro Ala Ser Pro Thr Ala
            420                 425                 430

Ser Pro Glu Pro Pro Pro Pro Glu
        435                 440


<210> SEQ ID NO 2
<211> LENGTH: 437
<212> TYPE: PRT
<213> ORGANISM: Mus sp.

<400> SEQUENCE: 2

Met Gly Leu Pro Gly Ser Pro Trp Gln Arg Val Leu Leu Leu Leu Gly
1               5                   10                  15

Leu Leu Leu Pro Pro Ala Thr Pro Phe Trp Leu Leu Asn Val Leu Phe
            20                  25                  30

Pro Pro His Thr Thr Pro Lys Ala Glu Leu Ser Asn His Thr Arg Pro
        35                  40                  45

Val Ile Leu Val Pro Gly Cys Leu Gly Asn Arg Leu Glu Ala Lys Leu
    50                  55                  60

Asp Lys Pro Asp Val Val Asn Trp Met Cys Tyr Arg Lys Thr Glu Asp
65                  70                  75                  80

Phe Phe Thr Ile Trp Leu Asp Phe Asn Leu Phe Leu Pro Leu Gly Val
                85                  90                  95

Asp Cys Trp Ile Asp Asn Thr Arg Ile Val Tyr Asn His Ser Ser Gly
            100                 105                 110

Arg Val Ser Asn Ala Pro Gly Val Gln Ile Arg Val Pro Gly Phe Gly
        115                 120                 125

Lys Thr Glu Ser Val Glu Tyr Val Asp Asp Asn Lys Leu Ala Gly Tyr
    130                 135                 140

Leu His Thr Leu Val Gln Asn Leu Val Asn Asn Gly Tyr Val Arg Asp
```

-continued

```
145                 150                 155                 160

Glu Thr Val Arg Ala Ala Pro Tyr Asp Trp Arg Leu Ala Pro His Gln
                165                 170                 175

Gln Asp Glu Tyr Tyr Lys Lys Leu Ala Gly Leu Val Glu Glu Met Tyr
            180                 185                 190

Ala Ala Tyr Gly Lys Pro Val Phe Leu Ile Gly His Ser Leu Gly Cys
        195                 200                 205

Leu His Val Leu His Phe Leu Leu Arg Gln Pro Gln Ser Trp Lys Asp
    210                 215                 220

His Phe Ile Asp Gly Phe Ile Ser Leu Gly Ala Pro Trp Gly Gly Ser
225                 230                 235                 240

Ile Lys Ala Met Arg Ile Leu Ala Ser Gly Asp Asn Gln Gly Ile Pro
                245                 250                 255

Ile Leu Ser Asn Ile Lys Leu Lys Glu Glu Gln Arg Ile Thr Thr Thr
            260                 265                 270

Ser Pro Trp Met Leu Pro Ala Pro His Val Trp Pro Glu Asp His Val
        275                 280                 285

Phe Ile Ser Thr Pro Asn Phe Asn Tyr Thr Val Gln Asp Phe Glu Arg
    290                 295                 300

Phe Phe Thr Asp Leu His Phe Glu Glu Gly Trp His Met Phe Leu Gln
305                 310                 315                 320

Ser Arg Asp Leu Leu Glu Arg Leu Pro Ala Pro Gly Val Glu Val Tyr
                325                 330                 335

Cys Leu Tyr Gly Gly Arg Pro Thr Pro His Thr Tyr Ile Tyr Asp His
            340                 345                 350

Asn Phe Pro Tyr Lys Asp Pro Val Ala Ala Leu Tyr Glu Asp Gly Asp
        355                 360                 365

Asp Thr Val Ala Thr Arg Ser Thr Glu Leu Cys Gly Gln Trp Gln Gly
    370                 375                 380

Arg Gln Ser Gln Pro Val His Leu Leu Pro Met Asn Glu Thr Asp His
385                 390                 395                 400

Leu Asn Met Val Phe Ser Asn Lys Thr Met Glu His Ile Asn Ala Ile
                405                 410                 415

Leu Leu Gly Ala Tyr Arg Thr Pro Lys Ser Pro Ala Ala Ser Pro Ser
            420                 425                 430

Pro Pro Pro Pro Glu
        435


<210> SEQ ID NO 3
<211> LENGTH: 440
<212> TYPE: PRT
<213> ORGANISM: Rattus sp.

<400> SEQUENCE: 3

Met Gly Leu Pro Gly Ser Pro Trp Gln Trp Val Leu Leu Leu Leu Gly
1               5                   10                  15

Leu Leu Leu Pro Pro Ala Thr Ser Phe Trp Leu Leu Asn Val Leu Phe
            20                  25                  30

Pro Pro His Thr Thr Pro Lys Ala Glu Leu Ser Asn His Thr Arg Pro
        35                  40                  45

Val Ile Leu Val Pro Gly Cys Met Gly Asn Arg Leu Glu Ala Lys Leu
    50                  55                  60

Asp Lys Pro Asn Val Val Asn Trp Leu Cys Tyr Arg Lys Thr Glu Asp
65                  70                  75                  80

Phe Phe Thr Ile Trp Leu Asp Phe Asn Met Phe Leu Pro Leu Gly Val
```

-continued

```
                85                  90                  95

Asp Cys Trp Ile Asp Asn Thr Arg Val Val Tyr Asn Arg Ser Ser Gly
            100                 105                 110

His Met Ser Asn Ala Pro Gly Val Gln Ile Arg Val Pro Gly Phe Gly
        115                 120                 125

Lys Thr Tyr Ser Val Glu Tyr Leu Asp Asp Asn Lys Leu Ala Gly Tyr
    130                 135                 140

Leu His Thr Leu Val Gln Asn Leu Val Asn Asn Gly Tyr Val Arg Asp
145                 150                 155                 160

Glu Thr Val Arg Ala Ala Pro Tyr Asp Trp Arg Leu Ala Pro Arg Gln
                165                 170                 175

Gln Asp Glu Tyr Tyr Gln Lys Leu Ala Gly Leu Val Glu Glu Met Tyr
            180                 185                 190

Ala Ala Tyr Gly Lys Pro Val Phe Leu Ile Gly His Ser Leu Gly Cys
        195                 200                 205

Leu His Val Leu His Phe Leu Leu Arg Gln Pro Gln Ser Trp Lys Asp
    210                 215                 220

His Phe Ile Asp Gly Phe Ile Ser Leu Gly Ala Pro Trp Gly Gly Ser
225                 230                 235                 240

Ile Lys Pro Met Arg Ile Leu Ala Ser Gly Asp Asn Gln Gly Ile Pro
                245                 250                 255

Ile Met Ser Asn Ile Lys Leu Arg Glu Glu Gln Arg Ile Thr Thr Thr
            260                 265                 270

Ser Pro Trp Met Phe Pro Ala His His Val Trp Pro Glu Asp His Val
        275                 280                 285

Phe Ile Ser Thr Pro Asn Phe Asn Tyr Thr Gly Gln Asp Phe Glu Arg
    290                 295                 300

Phe Phe Ala Asp Leu His Phe Glu Glu Gly Trp His Met Phe Leu Gln
305                 310                 315                 320

Ser Arg Asp Leu Leu Ala Gly Leu Pro Ala Pro Gly Val Glu Val Tyr
                325                 330                 335

Cys Leu Tyr Gly Val Gly Met Pro Thr Ala His Thr Tyr Ile Tyr Asp
            340                 345                 350

His Asn Phe Pro Tyr Lys Asp Pro Val Ala Ala Leu Tyr Glu Asp Gly
        355                 360                 365

Asp Asp Thr Val Ala Thr Arg Ser Thr Glu Leu Cys Gly Gln Trp Gln
    370                 375                 380

Gly Arg Gln Ser Gln Ala Val His Leu Leu Pro Met Asn Gly Thr Asp
385                 390                 395                 400

His Leu Asn Met Val Phe Ser Asn Lys Thr Leu Glu His Ile Asn Ala
                405                 410                 415

Ile Leu Leu Gly Ala Tyr Arg His Gly Thr Pro Lys Ser Pro Thr Ala
            420                 425                 430

Ser Leu Gly Pro Pro Thr Lys Glu
        435                 440
```

<210> SEQ ID NO 4
<211> LENGTH: 439
<212> TYPE: PRT
<213> ORGANISM: Artificial
<220> FEATURE:
<223> OTHER INFORMATION: Consensus LCAT polypeptide sequence
<220> FEATURE:
<221> NAME/KEY: MISC_FEATURE
<222> LOCATION: (3)..(3)
<223> OTHER INFORMATION: Xaa can be Pro or Leu
<220> FEATURE:

<221> NAME/KEY: MISC_FEATURE
<222> LOCATION: (10)..(10)
<223> OTHER INFORMATION: Xaa can be Trp or Arg
<220> FEATURE:
<221> NAME/KEY: MISC_FEATURE
<222> LOCATION: (12)..(12)
<223> OTHER INFORMATION: Xaa can be Thr or Leu
<220> FEATURE:
<221> NAME/KEY: MISC_FEATURE
<222> LOCATION: (23)..(23)
<223> OTHER INFORMATION: Xaa can be Ala or Thr
<220> FEATURE:
<221> NAME/KEY: MISC_FEATURE
<222> LOCATION: (59)..(59)
<223> OTHER INFORMATION: Xaa can be Gln or Arg
<220> FEATURE:
<221> NAME/KEY: MISC_FEATURE
<222> LOCATION: (88)..(88)
<223> OTHER INFORMATION: Xaa can be Leu or Phe
<220> FEATURE:
<221> NAME/KEY: MISC_FEATURE
<222> LOCATION: (90)..(90)
<223> OTHER INFORMATION: Xaa can be Met or Leu
<220> FEATURE:
<221> NAME/KEY: MISC_FEATURE
<222> LOCATION: (105)..(105)
<223> OTHER INFORMATION: Xaa can be Val or Ile
<220> FEATURE:
<221> NAME/KEY: MISC_FEATURE
<222> LOCATION: (109)..(109)
<223> OTHER INFORMATION: Xaa can be Arg or His
<220> FEATURE:
<221> NAME/KEY: MISC_FEATURE
<222> LOCATION: (113)..(113)
<223> OTHER INFORMATION: Xaa can be Leu or Arg
<220> FEATURE:
<221> NAME/KEY: MISC_FEATURE
<222> LOCATION: (131)..(131)
<223> OTHER INFORMATION: Xaa can be Tyr or Glu
<220> FEATURE:
<221> NAME/KEY: MISC_FEATURE
<222> LOCATION: (136)..(136)
<223> OTHER INFORMATION: Xaa can be Leu or Val
<220> FEATURE:
<221> NAME/KEY: MISC_FEATURE
<222> LOCATION: (138)..(139)
<223> OTHER INFORMATION: Amino acid at position 138 is Ser or Asp; Amino acid at position 139 is Ser or Asn
<220> FEATURE:
<221> NAME/KEY: MISC_FEATURE
<222> LOCATION: (173)..(173)
<223> OTHER INFORMATION: Xaa can be Glu or Ala
<220> FEATURE:
<221> NAME/KEY: MISC_FEATURE
<222> LOCATION: (175)..(175)
<223> OTHER INFORMATION: Xaa can be Gln or His
<220> FEATURE:
<221> NAME/KEY: MISC_FEATURE
<222> LOCATION: (178)..(178)
<223> OTHER INFORMATION: Xaa can be Glu or Gln
<220> FEATURE:
<221> NAME/KEY: MISC_FEATURE
<222> LOCATION: (182)..(182)
<223> OTHER INFORMATION: Xaa can be Arg or Lys
<220> FEATURE:
<221> NAME/KEY: MISC_FEATURE
<222> LOCATION: (192)..(192)
<223> OTHER INFORMATION: Xaa can be His or Tyr
<220> FEATURE:
<221> NAME/KEY: MISC_FEATURE
<222> LOCATION: (211)..(211)
<223> OTHER INFORMATION: Xaa can be His or Leu
<220> FEATURE:
<221> NAME/KEY: MISC_FEATURE
<222> LOCATION: (213)..(213)
<223> OTHER INFORMATION: Xaa can be Tyr or His
<220> FEATURE:
<221> NAME/KEY: MISC_FEATURE
<222> LOCATION: (221)..(221)
<223> OTHER INFORMATION: Xaa can be Ala or Ser
<220> FEATURE:
<221> NAME/KEY: MISC_FEATURE
<222> LOCATION: (225)..(225)
<223> OTHER INFORMATION: Xaa can be Arg or His
<220> FEATURE:
<221> NAME/KEY: MISC_FEATURE
<222> LOCATION: (243)..(243)
<223> OTHER INFORMATION: Xaa can be Pro or Ala
<220> FEATURE:
<221> NAME/KEY: MISC_FEATURE
<222> LOCATION: (245)..(246)
<223> OTHER INFORMATION: Amino acid at position 245 can be Leu or Arg;
Amino acid at position 246 can be Val or Ile
<220> FEATURE:
<221> NAME/KEY: MISC_FEATURE
<222> LOCATION: (258)..(258)
<223> OTHER INFORMATION: Xaa can be Met and Leu
<220> FEATURE:
<221> NAME/KEY: MISC_FEATURE
<222> LOCATION: (260)..(260)
<223> OTHER INFORMATION: Xaa can be Ser or Asn
<220> FEATURE:
<221> NAME/KEY: MISC_FEATURE
<222> LOCATION: (277)..(277)
<223> OTHER INFORMATION: Xaa can be Phe or Leu
<220> FEATURE:
<221> NAME/KEY: MISC_FEATURE
<222> LOCATION: (279)..(280)
<223> OTHER INFORMATION: Amino acid at position 279 can be Arg or Pro;
amino acid at position 280 can be Met or His
<220> FEATURE:
<221> NAME/KEY: MISC_FEATURE
<222> LOCATION: (293)..(293)
<223> OTHER INFORMATION: Xaa can be Ser or Asn
<220> FEATURE:
<221> NAME/KEY: MISC_FEATURE
<222> LOCATION: (299)..(299)
<223> OTHER INFORMATION: Xaa can be Arg or Gln
<220> FEATURE:
<221> NAME/KEY: MISC_FEATURE
<222> LOCATION: (302)..(302)
<223> OTHER INFORMATION: Xaa can be Gln or Glu
<220> FEATURE:
<221> NAME/KEY: MISC_FEATURE
<222> LOCATION: (306)..(306)
<223> OTHER INFORMATION: Xaa can be Ala or Thr
<220> FEATURE:
<221> NAME/KEY: MISC_FEATURE
<222> LOCATION: (315)..(315)
<223> OTHER INFORMATION: Xaa can be Tyr or Met
<220> FEATURE:
<221> NAME/KEY: MISC_FEATURE
<222> LOCATION: (317)..(317)
<223> OTHER INFORMATION: Xaa can be Trp or Phe
<220> FEATURE:
<221> NAME/KEY: MISC_FEATURE
<222> LOCATION: (325)..(326)
<223> OTHER INFORMATION: Amino acid at position 325 can be Ala or Glu;
amino acid at position 326 can be Gly or Arg
<220> FEATURE:
<221> NAME/KEY: MISC_FEATURE
<222> LOCATION: (342)..(342)
<223> OTHER INFORMATION: Xaa can be Leu or Arg
<220> FEATURE:
<221> NAME/KEY: MISC_FEATURE
<222> LOCATION: (346)..(346)
<223> OTHER INFORMATION: Xaa can be Arg or His
<220> FEATURE:
<221> NAME/KEY: MISC_FEATURE
<222> LOCATION: (353)..(353)
<223> OTHER INFORMATION: Xaa can be Gly or Asn
<220> FEATURE:
<221> NAME/KEY: MISC_FEATURE
<222> LOCATION: (357)..(357)
<223> OTHER INFORMATION: Xaa can be Thr or Lys
<220> FEATURE:
<221> NAME/KEY: MISC_FEATURE
<222> LOCATION: (361)..(362)
<223> OTHER INFORMATION: Amino acid at position 361 can be Gly or Ala;
amino acid at position 362 can be Val or Ala <220> FEATURE:
<221> NAME/KEY: MISC_FEATURE
<222> LOCATION: (381)..(381)
<223> OTHER INFORMATION: Xaa can be Leu or Gln
<220> FEATURE:
<221> NAME/KEY: MISC_FEATURE
<222> LOCATION: (387)..(387)
<223> OTHER INFORMATION: Xaa can be Pro or Ser
<220> FEATURE:
<221> NAME/KEY: MISC_FEATURE
<222> LOCATION: (395)..(398)
<223> OTHER INFORMATION: Amino acid at position 395 can be Leu or Met; Amino acid at position 396 can be His or Asn; Amino acid at position 397 can be Gly or Glu; Amino acid at position 398 can be Ile or Thr
<220> FEATURE:
<221> NAME/KEY: MISC_FEATURE
<222> LOCATION: (410)..(410)
<223> OTHER INFORMATION: Xaa can be Leu or Met
<220> FEATURE:
<221> NAME/KEY: MISC_FEATURE
<222> LOCATION: (427)..(427)
<223> OTHER INFORMATION: Xaa can be Ala or Lys
<220> FEATURE:
<221> NAME/KEY: MISC_FEATURE
<222> LOCATION: (430)..(430)
<223> OTHER INFORMATION: Xaa can be Thr or Ala
<220> FEATURE:
<221> NAME/KEY: MISC_FEATURE
<222> LOCATION: (434)..(434)
<223> OTHER INFORMATION: Xaa can be Glu or Ser
<220> FEATURE:
<221> NAME/KEY: MISC_FEATURE
<222> LOCATION: (439)..(439)
<223> OTHER INFORMATION: Xaa can be Glu or Cys

<400> SEQUENCE: 4

```
Met Gly Xaa Pro Gly Ser Pro Trp Gln Xaa Val Xaa Leu Leu Leu Gly
1               5                   10                  15

Leu Leu Leu Pro Pro Ala Xaa Pro Phe Trp Leu Leu Asn Val Leu Phe
            20                  25                  30

Pro Pro His Thr Thr Pro Lys Ala Glu Leu Ser Asn His Thr Arg Pro
        35                  40                  45

Val Ile Leu Val Pro Gly Cys Leu Gly Asn Xaa Leu Glu Ala Lys Leu
    50                  55                  60

Asp Lys Pro Asp Val Val Asn Trp Met Cys Tyr Arg Lys Thr Glu Asp
65                  70                  75                  80

Phe Phe Thr Ile Trp Leu Asp Xaa Asn Xaa Phe Leu Pro Leu Gly Val
                85                  90                  95

Asp Cys Trp Ile Asp Asn Thr Arg Xaa Val Tyr Asn Xaa Ser Ser Gly
            100                 105                 110

Xaa Val Ser Asn Ala Pro Gly Val Gln Ile Arg Val Pro Gly Phe Gly
        115                 120                 125

Lys Thr Xaa Ser Val Glu Tyr Xaa Asp Xaa Xaa Lys Leu Ala Gly Tyr
    130                 135                 140

Leu His Thr Leu Val Gln Asn Leu Val Asn Asn Gly Tyr Val Arg Asp
145                 150                 155                 160

Glu Thr Val Arg Ala Ala Pro Tyr Asp Trp Arg Leu Xaa Pro Xaa Gln
                165                 170                 175

Gln Xaa Glu Tyr Tyr Xaa Lys Leu Ala Gly Leu Val Glu Glu Met Xaa
            180                 185                 190

Ala Ala Tyr Gly Lys Pro Val Phe Leu Ile Gly His Ser Leu Gly Cys
        195                 200                 205

Leu His Xaa Leu Xaa Phe Leu Leu Arg Gln Pro Gln Xaa Trp Lys Asp
    210                 215                 220
```

-continued

```
Xaa Phe Ile Asp Gly Phe Ile Ser Leu Gly Ala Pro Trp Gly Gly Ser
225                 230                 235                 240

Ile Lys Xaa Met Xaa Xaa Leu Ala Ser Gly Asp Asn Gln Gly Ile Pro
                245                 250                 255

Ile Xaa Ser Xaa Ile Lys Leu Lys Glu Glu Gln Arg Ile Thr Thr Thr
            260                 265                 270

Ser Pro Trp Met Xaa Pro Xaa Xaa Ala Trp Pro Glu Asp His Val Phe
        275                 280                 285

Ile Ser Thr Pro Xaa Phe Asn Tyr Thr Gly Xaa Asp Phe Xaa Arg Phe
    290                 295                 300

Phe Xaa Asp Leu His Phe Glu Glu Gly Trp Xaa Met Xaa Leu Gln Ser
305                 310                 315                 320

Arg Asp Leu Leu Xaa Xaa Leu Pro Ala Pro Gly Val Glu Val Tyr Cys
                325                 330                 335

Leu Tyr Gly Val Gly Xaa Pro Thr Pro Xaa Thr Tyr Ile Tyr Asp His
            340                 345                 350

Xaa Phe Pro Tyr Xaa Asp Pro Val Xaa Xaa Leu Tyr Glu Asp Gly Asp
        355                 360                 365

Asp Thr Val Ala Thr Arg Ser Thr Glu Leu Cys Gly Xaa Trp Gln Gly
    370                 375                 380

Arg Gln Xaa Gln Pro Val His Leu Leu Pro Xaa Xaa Xaa Xaa Gln His
385                 390                 395                 400

Leu Asn Met Val Phe Ser Asn Leu Thr Xaa Glu His Ile Asn Ala Ile
                405                 410                 415

Leu Leu Gly Ala Tyr Arg Gln Gly Pro Pro Xaa Ser Pro Xaa Ala Ser
            420                 425                 430

Pro Xaa Pro Pro Pro Pro Xaa
        435
```